United States Patent
Mullaly et al.

(10) Patent No.: US 9,314,318 B2
(45) Date of Patent: Apr. 19, 2016

(54) DENTAL ANCHOR APPARATUS AND METHOD

(75) Inventors: Scott Mullaly, San Marcos, CA (US); Paul T. Zuest, Valley Center, CA (US)

(73) Assignee: ZEST IP HOLDINGS, LLC, Escondido, CA (US)

(*) Notice: Subject to any disclaimer, the term of this patent is extended or adjusted under 35 U.S.C. 154(b) by 159 days.

(21) Appl. No.: 12/537,863

(22) Filed: Aug. 7, 2009

(65) Prior Publication Data

US 2010/0055645 A1 Mar. 4, 2010

Related U.S. Application Data

(60) Provisional application No. 61/091,982, filed on Aug. 26, 2008, provisional application No. 61/138,817, filed on Dec. 18, 2008.

(51) Int. Cl.
*A61C 8/00* (2006.01)
*A61C 13/265* (2006.01)

(52) U.S. Cl.
CPC ............. *A61C 8/0075* (2013.01); *A61C 8/0025* (2013.01); *A61C 8/0066* (2013.01);
(Continued)

(58) Field of Classification Search
CPC .. A61C 13/265; A61C 13/2656; A61C 8/006; A61C 8/0062; A61C 8/0066; A61C 8/0069; A61C 8/0074; A61C 8/0075; A61C 8/0078; A61C 8/0095; A61C 8/0096; A61C 8/0098; A61C 8/0025
USPC .......... 433/172–177, 201.1, 215; 623/116.11, 623/17.17, 23.5; 427/2.26, 2.29, 2.1; 606/73
See application file for complete search history.

(56) References Cited

U.S. PATENT DOCUMENTS 711,324 A 10/1902 Lacy
866,340 A 9/1907 Roach
(Continued)

FOREIGN PATENT DOCUMENTS

| DE | 3403448 | 2/1984 |
| EP | 0037864 | 10/1981 |
| WO | WO 89/06941 | 8/1989 |

OTHER PUBLICATIONS

International Search Report and Written Opinion from related PCT/US2009/053363 dated Oct. 8, 2009.
(Continued)

*Primary Examiner* — Cris L Rodriguez
*Assistant Examiner* — Mirayda A Aponte
(74) *Attorney, Agent, or Firm* — Procopio, Cory, Hargreaves & Savitch LLP; Noel C. Gillespie

(57) ABSTRACT

A dental anchor apparatus having a one or two part endosseous implant securable in a patient's mouth and a retention member which is releasably engageable with the implant. The implant has an abutment head at one end and a threaded post projecting from the head and designed for threaded engagement in the jaw bone, the head having an outer locating surface portion. The retention member is generally cup-shaped with a first end and a peripheral skirt extending from the first end to form a cavity, the skirt having an inner locating surface which is engaged over the outer locating surface portion of the head. The head may also have a socket in which a post extending from an inner end of the retention member engages as the parts are moved into releasable snap engagement.

10 Claims, 24 Drawing Sheets

(52) U.S. Cl.
CPC ............. *A61C 8/0069* (2013.01); *A61C 8/0074* (2013.01); *A61C 8/0096* (2013.01); *A61C 8/0098* (2013.01); *A61C 13/265* (2013.01); *A61C 13/2656* (2013.01); *A61C 8/006* (2013.01); *A61C 8/0062* (2013.01); *A61C 8/0078* (2013.01); *A61C 8/0095* (2013.01)

(56) References Cited

U.S. PATENT DOCUMENTS

| | | | |
|---|---|---|---|
| 3,514,858 A | 6/1970 | Silverman | |
| 3,787,975 A | 1/1974 | Zuest | |
| 3,991,472 A | 11/1976 | Lukesch | |
| 4,158,256 A | 6/1979 | Wiland et al. | |
| 4,290,755 A | 9/1981 | Scott | |
| 4,431,416 A | 2/1984 | Niznick | |
| 4,488,874 A | 12/1984 | Soifer | |
| 4,488,875 A | 12/1984 | Niznick | |
| 4,540,367 A | 9/1985 | Sulc | |
| 4,547,156 A | 10/1985 | Hader | |
| 4,626,213 A | 12/1986 | Shiner et al. | |
| 4,645,453 A | 2/1987 | Niznick | |
| 4,657,510 A | 4/1987 | Gittleman | |
| 4,738,623 A | 4/1988 | Driskell | |
| 4,780,080 A | 10/1988 | Haris | |
| 4,793,808 A | 12/1988 | Kirsch | |
| 4,832,601 A | 5/1989 | Linden | |
| 4,854,872 A | 8/1989 | Detsch | |
| 4,907,969 A | 3/1990 | Ward | |
| 4,932,868 A * | 6/1990 | Linkow et al. | 433/174 |
| 4,934,935 A | 6/1990 | Edwards | |
| 4,957,438 A | 9/1990 | Bax | |
| 4,988,297 A | 1/1991 | Lazzara et al. | |
| 5,007,835 A | 4/1991 | Valen | |
| 5,030,095 A | 7/1991 | Niznick | |
| 5,092,770 A | 3/1992 | Zakula | |
| 5,120,222 A | 6/1992 | Sulc | |
| 5,194,000 A | 3/1993 | Dury | |
| 5,195,891 A | 3/1993 | Sulc | |
| 5,211,561 A | 5/1993 | Graub | |
| 5,417,570 A * | 5/1995 | Zuest et al. | 433/177 |
| 5,520,540 A | 5/1996 | Nardi et al. | |
| 5,556,280 A | 9/1996 | Pelak | |
| 5,636,989 A | 6/1997 | Somborac | |
| 5,678,997 A | 10/1997 | De Buck | |
| 5,873,721 A * | 2/1999 | Willoughby | 433/173 |
| 5,997,300 A | 12/1999 | Tseng | |
| 6,030,219 A | 2/2000 | Zuest et al. | |
| 6,299,447 B1 | 10/2001 | Zuest et al. | |
| 6,302,693 B1 | 10/2001 | Mena | |
| 6,375,465 B1 * | 4/2002 | Engman et al. | 433/174 |
| 6,695,616 B2 | 2/2004 | Ellison | |
| 6,716,030 B1 | 4/2004 | Bulard et al. | |
| 6,726,480 B1 * | 4/2004 | Sutter | 433/173 |
| 6,827,575 B1 * | 12/2004 | Jorneus | 433/174 |
| 6,981,871 B2 * | 1/2006 | Mullaly et al. | 433/172 |
| 6,981,873 B2 * | 1/2006 | Choi et al. | 433/173 |
| 7,090,494 B2 * | 8/2006 | Shelemay et al. | 433/173 |
| 7,281,924 B2 | 10/2007 | Ellison | |
| 2002/0120275 A1 | 8/2002 | Schmieding et al. | |
| 2004/0005530 A1 | 1/2004 | Mullaly | |
| 2005/0042574 A1 * | 2/2005 | Lazarof | 433/174 |
| 2006/0183078 A1 * | 8/2006 | Niznick | 433/173 |
| 2007/0275351 A1 * | 11/2007 | Park et al. | 433/174 |
| 2008/0153063 A1 | 6/2008 | Mullaly et al. | |
| 2009/0048633 A1 * | 2/2009 | Eom et al. | 606/301 |
| 2009/0305193 A1 * | 12/2009 | Han et al. | 433/174 |
| 2010/0143869 A1 * | 6/2010 | Padros Fradera | 433/174 |

OTHER PUBLICATIONS

The Stern Era. A New Era in Attachment Dentistry Brochure, APM-Sterngold, 1990.
Zest Anchors. Presenting the new Locator Implant Attachment brochure, Dec. 14, 2000.
Australian Patent Application No. 2009285941; Examination Report dated Jun. 25, 2014.
Office Action for Canadian Application No. 2734644, dated May 14, 2015 (3 pages).
Communication Pursuant to Article 94(3) EPC; dated Jun. 2, 2015 for European Application No. 09810442.5-1659.

* cited by examiner

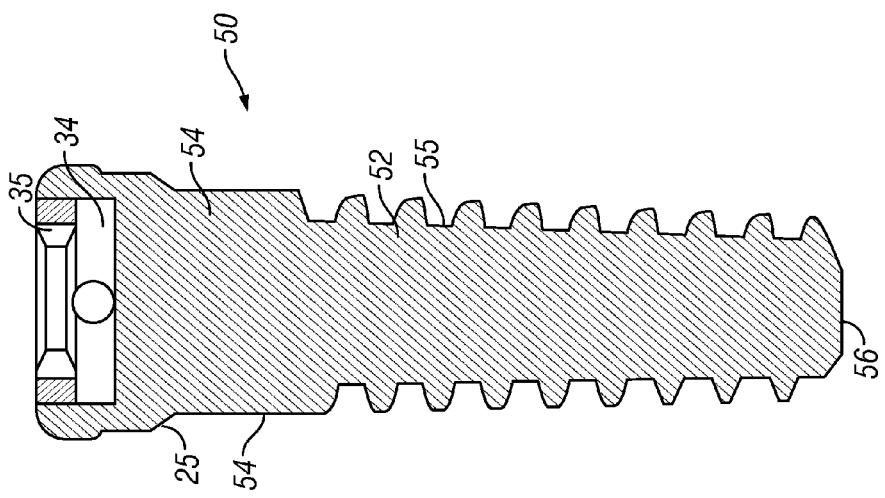
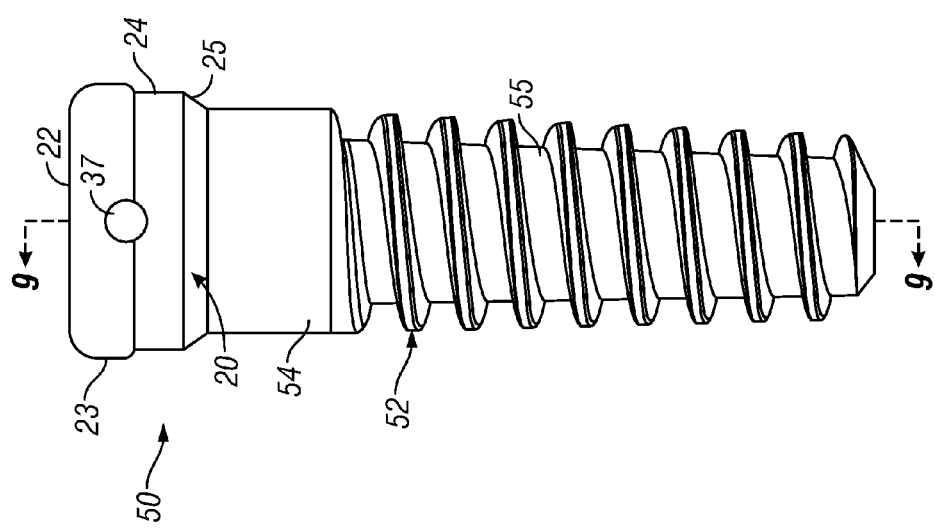

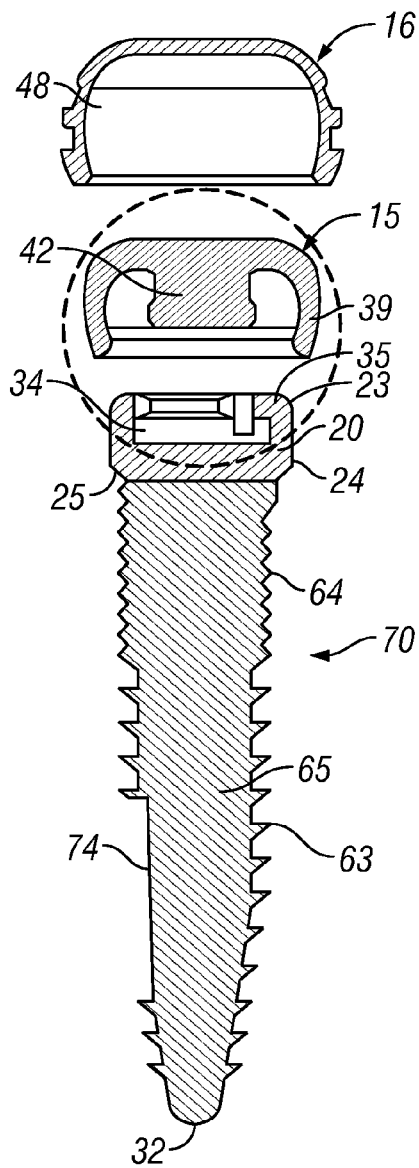
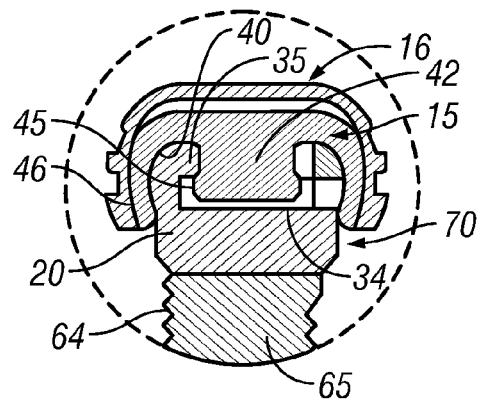
FIG. 13
FIG. 14

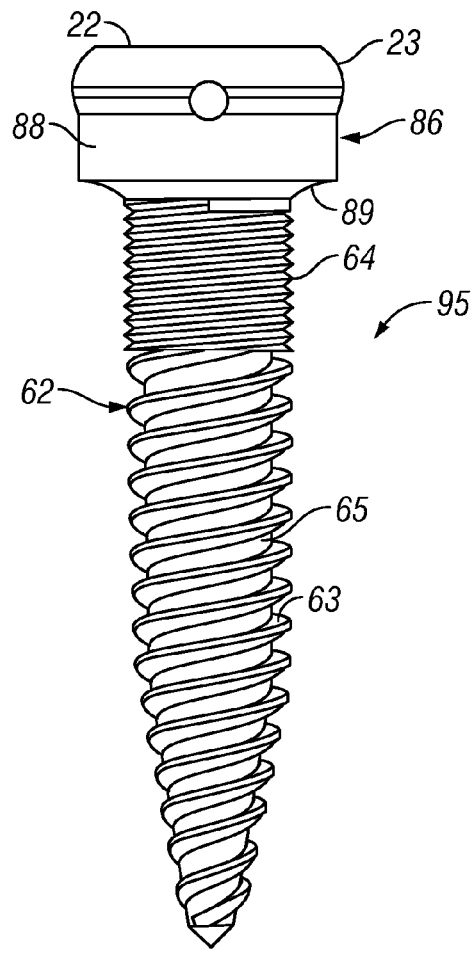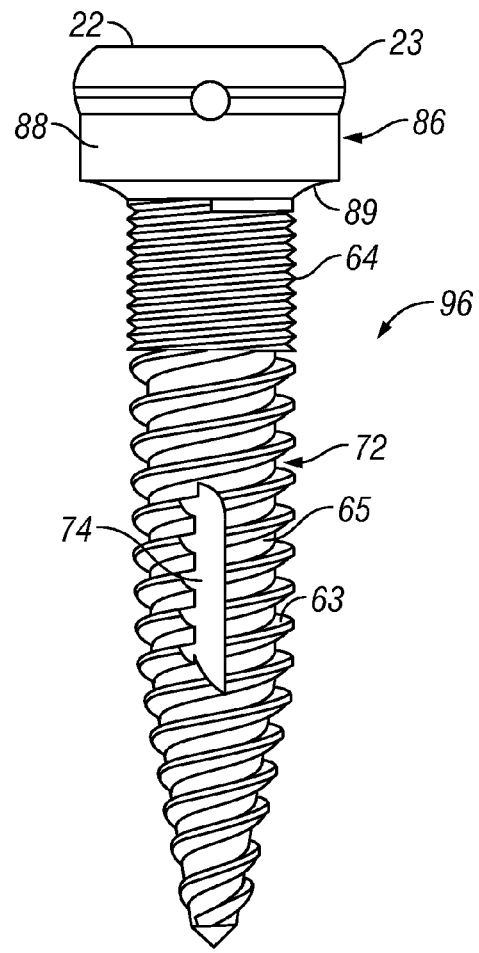
*FIG. 20*  *FIG. 21*

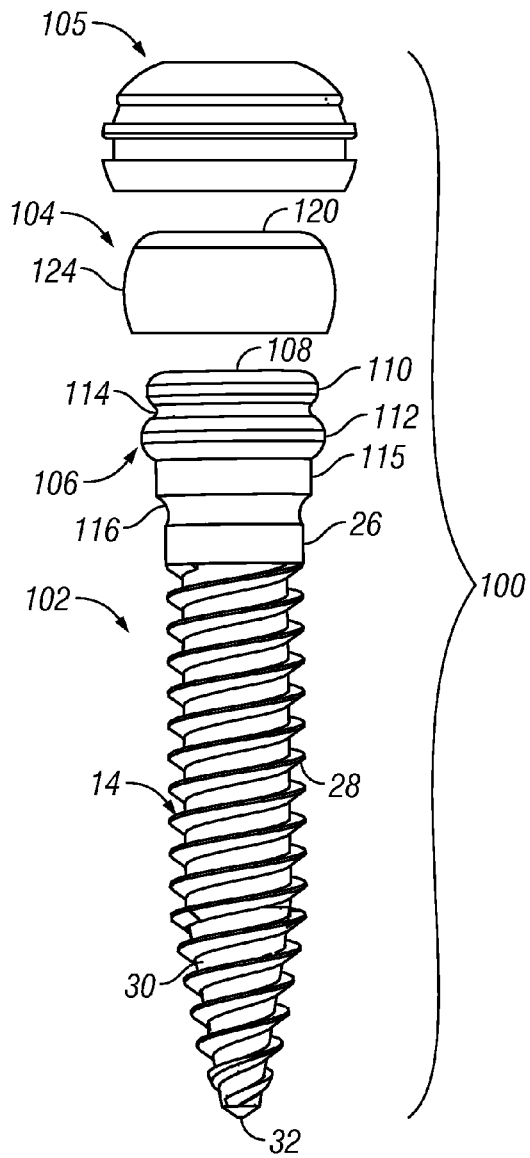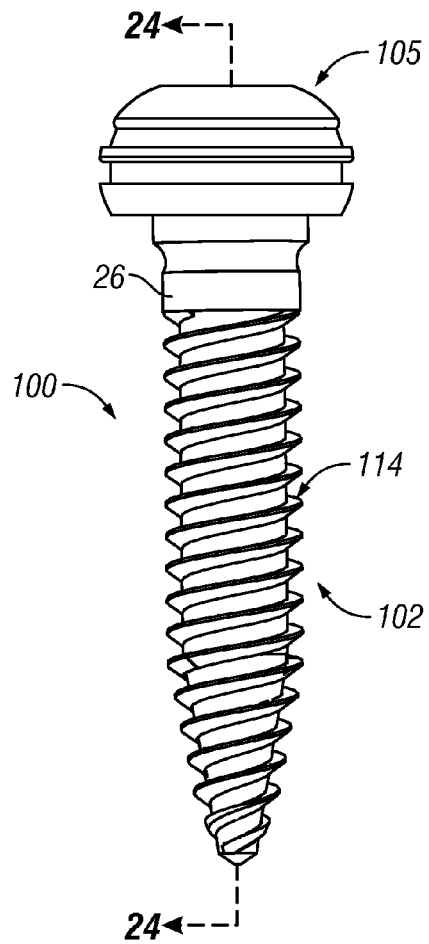
FIG. 22
FIG. 23

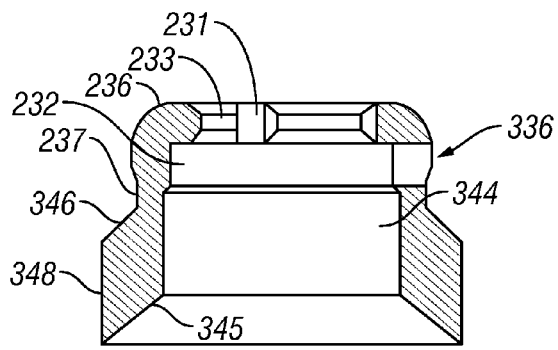
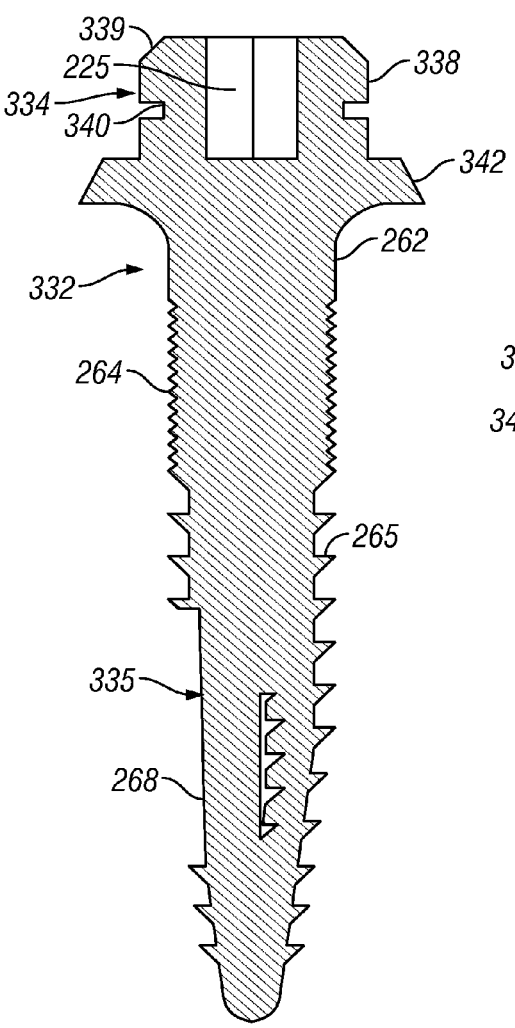
FIG. 42
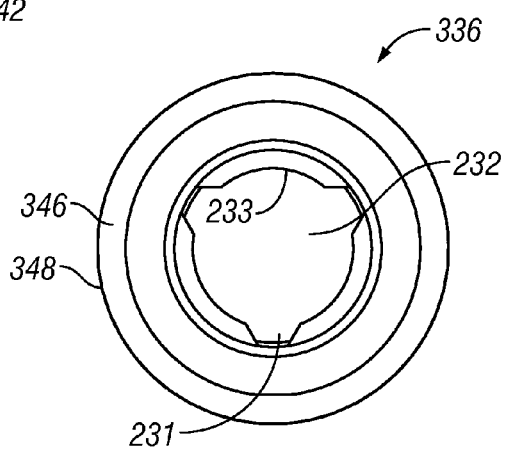
FIG. 43
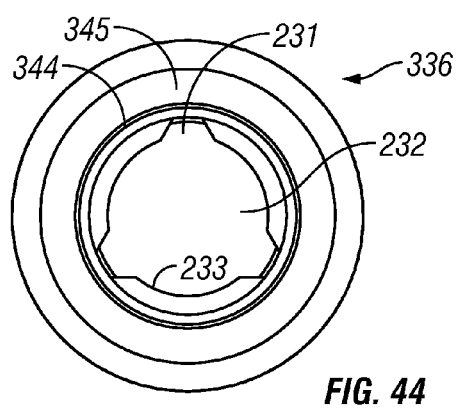
FIG. 44

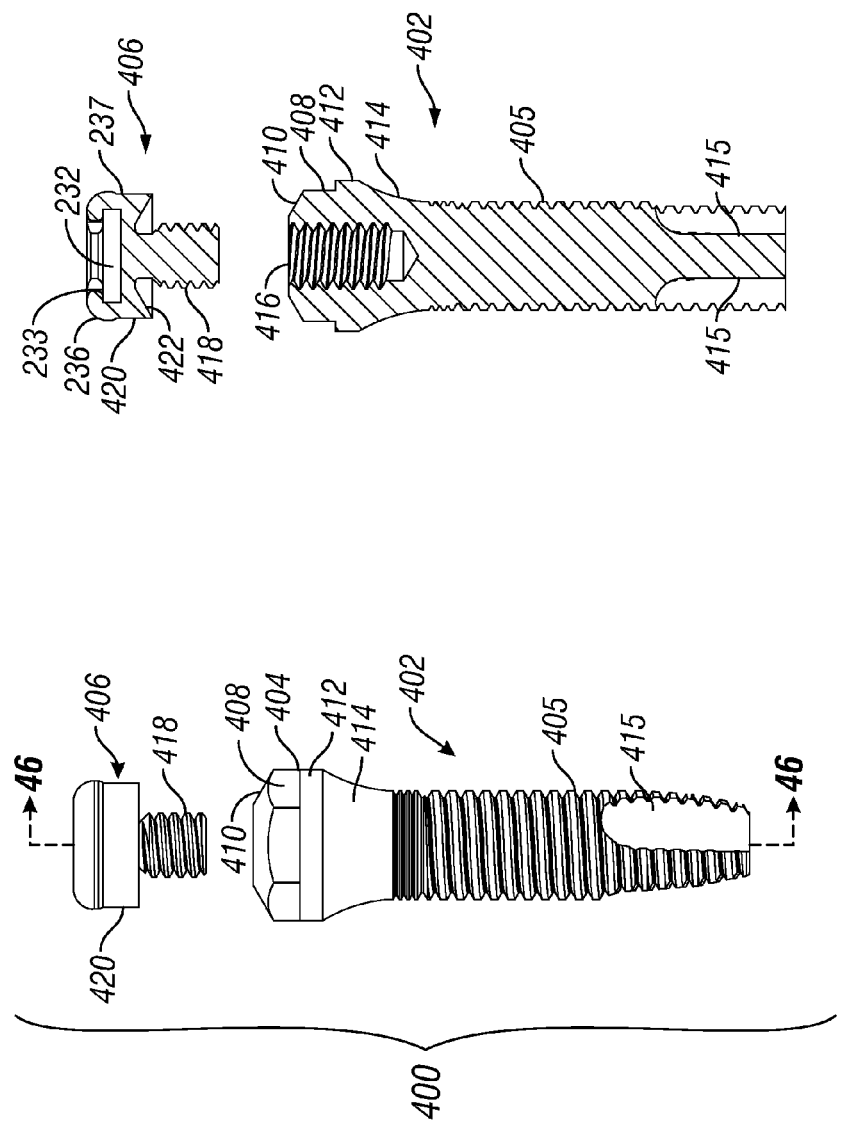

US 9,314,318 B2

DENTAL ANCHOR APPARATUS AND METHOD

RELATED APPLICATION

The present application claims the benefit of co-pending U.S. provisional patent application No. 61/091,982 filed Aug. 26, 2008, and co-pending U.S. provisional patent application No. 61/138,817 filed Dec. 18, 2008, the contents of each of which are incorporated herein by reference in their entirety.

BACKGROUND

1. Field of the Invention

The present invention relates to an apparatus and method for anchoring a dental appliance, and is particularly concerned with a mini or endosseous implant assembly and method.

2. Related Art

Various systems and methods are known for attaching a dental prosthesis such as a full or partial denture or the like in a patient's jaw. Such systems generally comprise mating male and female parts, one of which is attached to the dental prosthesis and the other of which comprises an abutment which is mounted at a selected position in the patient's jaw. The abutment may be attached to a root, an endosseous implant, or an adjacent tooth, or in some cases may be inserted directly in the jaw bone.

SUMMARY

Embodiments described herein provide for dental anchor apparatus having an implant device with an abutment head for snap engagement with a mating retention member engaged in a recess in a dental appliance, and a threaded post extending from the head for threaded engagement with bone. In one embodiment, the abutment head is formed integrally with the post to provide a one-piece endosseous implant. In alternative embodiments, the implant device is in two parts, comprising the abutment head and the main body of the implant, and the abutment head is releasably attached to the main body.

According to one embodiment, a dental anchor apparatus comprises an endosseous implant securable in a patient's mouth and a retention member which is releasably engageable with the implant. The implant has an abutment head at one end and a threaded post projecting from the head for threaded engagement in bone, the head having at least an outer locating surface portion. The retention member is generally cup-shaped with a first end and a peripheral skirt extending from the first end to form a cavity, the skirt having an inner locating surface which is engaged over the outer locating surface portion of the head. The retention member is designed for swivel engagement in a cap secured in a recess in a dental appliance.

In one embodiment, the inner locating surface of the skirt and the outer locating surface portion of the head have interengageable snap formations and the retention member is releasably snap engaged over the head. In another embodiment, the head has an inwardly extending socket which comprises a second locating portion and the retention member has a post extending from the first end inside the skirt which engages in the socket when the retention member is snap engaged with the socket. The post may be used for alignment purposes. In one embodiment, the socket and post have interengageable snap formations to provide an inner snap engagement between the abutment and retention member. Both an inner snap engagement between the post and socket and an outer snap engagement between the cavity and outer locating portion of the head may be provided in some embodiments, while in others only an inner or outer snap engagement is provided.

In some embodiments, the abutment head is formed integrally with the remainder of the body of the implant to provide a one-piece endosseous implant, while in other embodiments the abutment head is formed separately and releasably attached to the main body of the implant. In the latter case, the abutment head can be removed from the implant body and replaced with a new head when the locating surface portions become too worn to function properly, rather than replacing the entire implant.

In another embodiment, the outer locating surface on the head has a first set of at least two axially spaced snap engaging formations while the inner locating surface of the retention member has a second set of at least two axially spaced snap engaging formations for releasable snap engagement with the snap engaging formations on the head. One of the sets of snap engaging formations may comprises spaced annular projections or ribs on one of the locating surfaces while the other set comprises spaced annular grooves for snap engagement over the annular projections or ribs. The post may be omitted in this embodiment, or the post may be included for additional assistance in aligning the dental appliance when placed in the mouth.

In one embodiment, the apparatus includes a cap which is secured in a recess in a dental appliance and which is designed to engage over the retention member, the cap and retention member having respective rounded inner and outer surfaces for swivel engagement of the retention member in the cap. The swiveling engagement of the retention member in the cap allows for a swiveling, rotational movement or hinging movement between the cap and retention member. This allows minor corrections for non-parallel abutments and reduces wear, as described in U.S. Pat. Nos. 6,030,219 and 6,299,447, the contents of which are incorporated herein by reference.

According to one embodiment, a two piece endosseous implant for a dental attachment assembly comprises a main body having a first end portion and a threaded shaft extending from the first end portion for threaded engagement in the jaw bone, and an abutment head or member designed for removable attachment to the main body of the implant. The abutment member has locating portion designed for releasable snap engagement with the denture component or snap engaging part which is positioned in the denture.

In a first embodiment of a two-piece endosseous implant, the first end portion of the main body has external threads which engage internal threads in the abutment member or head. In an alternative embodiment, the abutment head has a shaft or post with external threads which engage internal threads in a bore in the first end portion of the main body. In both of these alternatives, a tool may be provided for removal of the abutment head while holding the main body of the implant in place. In one embodiment, the tool has a lower hex portion which engages in an internal hex in the main body of the implant, while a driver portion which is rotatable relative to the lower hex portion engages with drive engaging portions in the locator or abutment head to unthread the abutment head from the main body. Alternatively, the abutment head and main body may be designed with mating, taper press fit portions instead of threaded engagement portions.

In both the one-piece and two-piece implants, the threaded post or shaft is adapted to be implanted directly in a prepared bore in a patient's jaw bone, and may be designed for osseointegration with the patient's jaw bone. The implant may be of so-called "mini-implant" dimensions having a maximum head diameter of the order of 1.5 mm. to 4.0 mm, and the threaded post having a maximum thread diameter slightly less than the head diameter. The threaded post or shaft may be provided in a range of different lengths for selection based on the available implantation depth in a patient's jaw bone. In one embodiment, the threaded post of the implant has a first portion of uniform outer diameter and a second portion extending from the first portion to the end of the screw which is of gradually tapered diameter. The threaded post may have a single lead thread, a double lead thread, or other multiple lead threads, or dual threads of different pitch, and may have opposing axial cuts for self-tapping into a bone, so as to create threads in the bone as the threaded post is engaged in a bore in the bone. A double, triple or quadruple lead thread allows for quick and solid engagement into a tapped bone site. The projecting screw threads form an undercut region and bone growth and attachment in this area increases the strength of the attachment and resistance to loosening forces.

In alternative embodiments, the threaded post may be designed for optional later removal from the jaw bone for replacement purposes. In this case, the post may have a simple thread with no axial cuts. Instead of the threaded post, other formations may be provided on the post for engagement with mating attachment formations in a prepared bore in the jaw bone or the like.

The implant may have a cuff area between the abutment head and post. In the case of a two-piece implant, the cuff area may be located entirely on the first end portion of the main body, or entirely on the abutment head, or partly on the first end portion and partly on the head. In each case, different implants may be provided with cuff areas in different heights to accommodate different tissue heights. The line of connection or separation between the first end portion of the main body and the abutment head may be designed to be above the tissue or gum level, so that the abutment head may be removed by a dentist without any disturbance of the tissue.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 8 is an enlarged side elevation view of an endosseous implant similar to the implant of FIGS. 1 to 7 but with a modified threaded post for use in place of the post of FIGS. 1 to 7;

FIG. 9 is a cross-sectional view on the lines 9-9 of FIG. 8;

FIG. 13 is an exploded cross-sectional view of an anchor apparatus similar to FIG. 1 but using the modified implant of FIGS. 11 and 12;

FIG. 14 is an enlarged view of the circled part of the anchor apparatus of FIG. 13 in an assembled condition;

FIG. 20 is a side elevation view of an endosseous implant similar to the implant in the apparatus of FIGS. 15 to 19 but with a modified threaded post;

FIG. 21 is a side elevation view of an implant similar to the implant of FIG. 20 but with another modified threaded post;

FIG. 22 is an exploded side elevation view of a dental anchor apparatus according to another embodiment;

FIG. 23 is a side elevation view of the dental anchor apparatus of FIG. 22 with the parts assembled;

FIG. 42 is a cross-sectional view of the implant parts on the line 42-42 of FIG. 41;

FIG. 43 is a top plan view of the abutment head of the two part implant of FIGS. 41 and 42; and FIG. 44 is a bottom plan view of the abutment head of FIG. 43

FIG. 45 is an exploded side elevation view of another modified two part mini implant according to another embodiment, with the parts of the implant separated;

FIG. 46 is a longitudinal cross-sectional view of the parts on the line 46-46 of FIG. 45;

DETAILED DESCRIPTION

Figure 2:
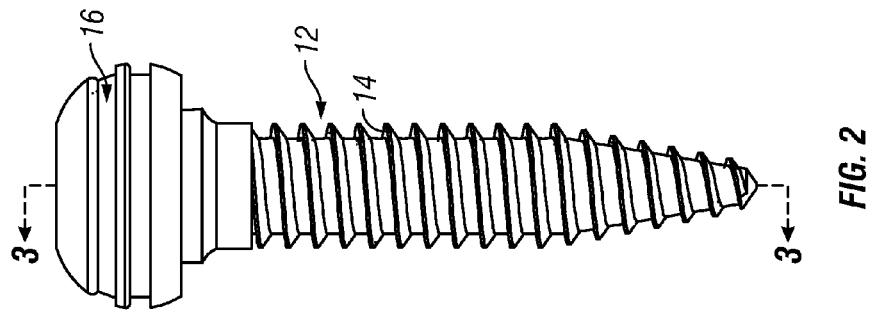
FIG. 2 is an enlarged side elevation view of the dental anchor of FIG. 1, with the parts assembled together.

Certain embodiments as disclosed herein provide for a dental attachment or anchor apparatus having an endosseous implant which has an abutment head and a post extending from the head for direct engagement in a patient's jaw bone, and a retention member designed for snap engagement over the head of the implant and for swivel engagement in a cap secured in a dental appliance or prosthesis. The retention member and implant have interengageable snap engagement formations for releasably retaining the dental appliance or prosthesis on the implant member. In an installation, a plurality of spaced implants are implanted in the jaw bone and retention members engaged in correspondingly spaced caps secured in the dental appliance are snap engaged with the abutment heads of the respective implants to retain the dental appliance in position in a patient's mouth.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention.

In the following description, the terms "upper" and "lower" are used to denote locations of various portions of the implant as seen in the drawings, and are not intended to indicate which ends are uppermost when the implant is installed in the jaw, which is dependent on whether the implant is located in the upper or lower jaw.

Figures 3, 4:
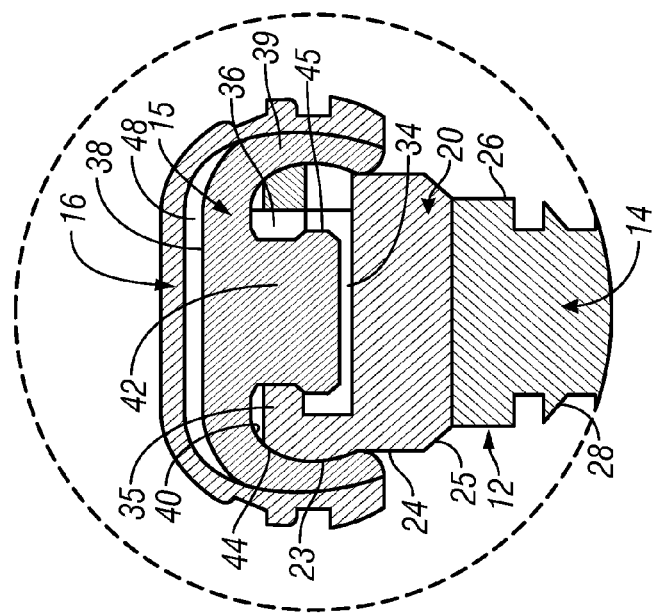
FIG. 3 is a cross-sectional view of the apparatus on the lines 3-3 of FIG. 2, on a smaller scale than in FIGS. 1 and 2, which illustrates the anchor assembly secured in a patient's jaw bone with the cap positioned in a denture or dental appliance.
FIG. 4 is an exploded sectional view of the circled portion of the apparatus in FIG. 3, illustrating the snap engagement between the head of the implant and the retention member.
Figure 6:
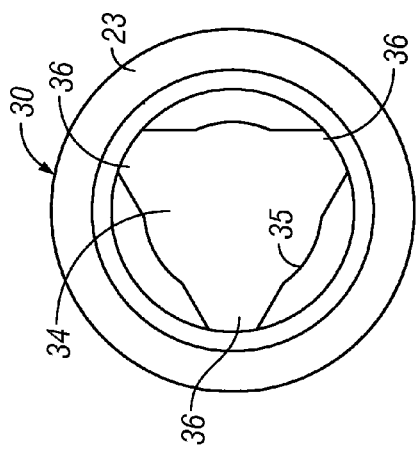
FIG. 6 is an enlarged top plan view of the implant of FIGS. 1 to 4.

FIGS. 1 to 7 illustrate a first embodiment of a dental attachment or anchor apparatus 10 comprising a one-piece implant 12 with an abutment head or head portion 20 and an integral threaded post or shaft 14, a retention member 15 for releasable snap engagement with the head 20 of implant 12, and a cap 16 designed to be secured in an indent in a dental appliance 18 such as an overdenture, a partial denture, or the like, as illustrated in FIG. 3. Implant 12 is of relatively strong material such as coated titanium or other standard materials generally used for dental anchors or abutments, and the threaded post 14 is designed for direct engagement in a prepared bore in endosseous bone 100, as indicated in FIG. 3.

Head 20 has a generally flat first end 22, and an outer curved or bulbous locating portion 23 extending from first end. A generally cylindrical portion or cuff portion 24 extends from the end of locating portion 23, and an inwardly tapered rim portion 25 extends from first cylindrical portion 24. Implants may be made with cuff portions of different heights to accommodate patients with different tissue heights. In this embodiment, threaded post or shaft 14 has a short cylindrical portion 26 extending from rim portion 25, and single thread 28 extending along the remainder of the length of the post or shaft 14. Post 14 has an inwardly tapered end portion 30 extending up to the tip 32 of the post.

Figure 1:
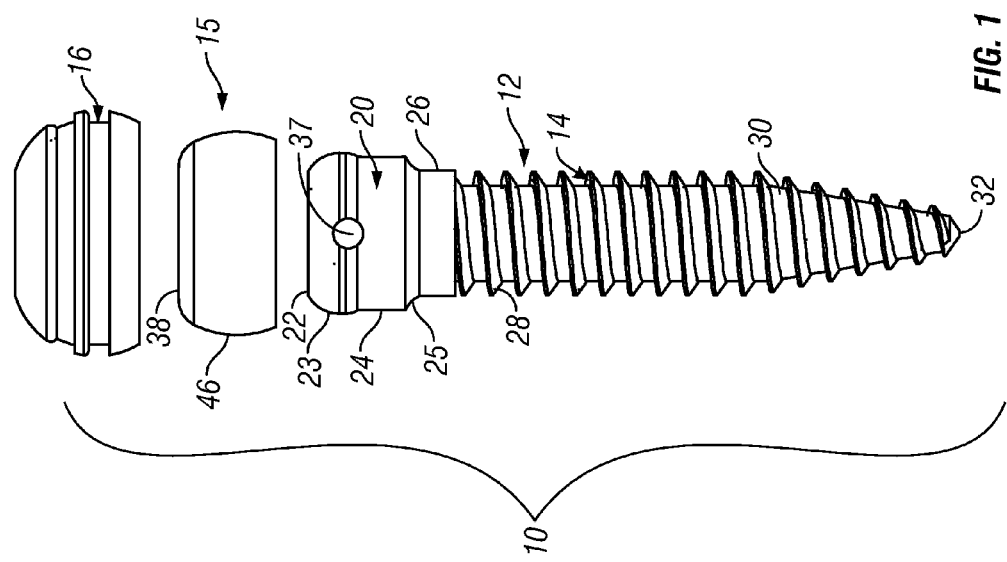
FIG. 1 is an enlarged view of a dental anchor apparatus according to a first embodiment, with the parts of the apparatus separated.

FIGS. 2 to 4 illustrate the parts of FIG. 1 assembled together, with the retention member 15 in hinging, snap engagement in cap 16 and releasably snap engaged over the locating portion 23 of head 20. FIG. 3 illustrates the operative condition of the parts, with cap 16 installed in a suitable cavity in a dental appliance or prosthesis 18, and the threaded post 14 in threaded engagement in a prepared bore in jaw bone 100. The threaded post may be coated by any suitable coating material prior to installation, as is known in the field of endosseous implants.

Figure 5:
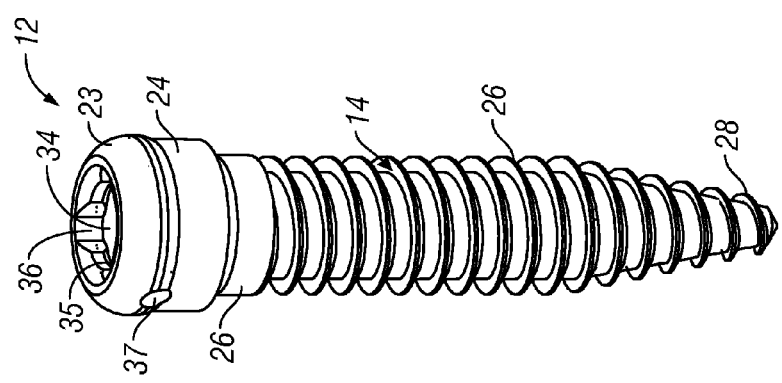
FIG. 5 is a perspective view of the endosseous implant of the apparatus of FIGS. 1 to 4.

As illustrated in FIGS. 3 to 6, the head 20 of implant 12 has a socket 34 extending from flat end face 22 through part of the length of the head, and has an inwardly extending rounded rim 35 at the outer end of the socket. Rim 35 has cut-outs 36, as seen in FIGS. 4 and 5, for receiving the end of a suitable tool for securing the threaded post in a prepared bore in a patient's jaw bone. One or more weep holes 37 are provided through the wall of the socket, as seen in FIG. 4, to allow saliva to escape from the socket.

Figure 7:
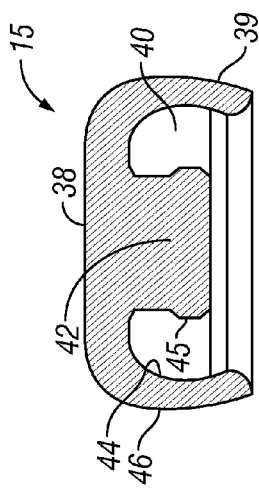
FIG. 7 is an enlarged cross-sectional view of the retention member in the anchor apparatus of FIGS. 1 to 6.

As best illustrated in FIG. 7, the retention member 15 is generally cup-shaped with a generally flat first end 38, an outer skirt 39 extending from first end 38 defining an internal cavity 40 for engagement over the head 20, and a retention pin or post 42 extending from end 38 inside the cavity for engagement in socket 34, as seen in FIGS. 3 and 4. Retention member 15 is made of a material having some resilience, such as nylon or plastic material. Retention member 15 may be similar to the retention or male elements as described in U.S. Pat. Nos. 6,030,219 and 6,299,447 of Zuest et al., the contents of which are incorporated herein by reference. The skirt 39 has a concave inner surface or locating portion 44 designed for snap engagement over the outer locating portion. The retention pin or post 42 has an enlarged end portion 45 (FIG. 4) of slightly larger diameter than the remainder of the post, and slightly smaller diameter than the inner diameter of socket rim 35, with the rim 35 and end portion 45 comprising snap engaging formations. As the skirt 39 engages over outer locating portion 23 of the head, the end of post 42 is compressed slightly as it is forced through the opening defined by socket rim 35, and then expands so that it is releasably retained in the socket. Similarly, the outer end of skirt 38 is expanded as it is forced over the bulbous or rounded surface of locating portion 23, then snaps back to engage the end of locating portion 23. Thus, the locating portion 23 and inner concave surface of skirt 38 comprise a second set of snap engaging formations between the retention member 15 and the head 20 of abutment member 12.

The outer surface 46 of the retention member 15 is convex or rounded for snap-fit, swiveling engagement in a cavity 48 of corresponding shape in the cap 16, as illustrated in FIGS. 3 and 4. The swivel joint formed between the retention member and cap is similar or identical to that described in U.S. Pat. Nos. 6,030,219 and 6,299,447 referenced above. The pivoting of the nylon or plastic resilient retention or male member 15 in the metal denture cap 16 allows minor corrections for non parallel abutments as well as providing a longer lasting, resilient connection.

In one embodiment, the anchor apparatus is made in a range of different sizes for selection by a dental surgeon or dentist based on the size of a patient's jaw and the available tissue and bone depth and thickness. The implant or abutment member may be provided in a similar size range to so-called mini abutment members or mini implants. In one embodiment, heads 20 are provided in a range of diameters from around 1.5 mm. to 4.0 mm., while the length of the threaded post may be in the range from around 6 mm. to 21 mm. A plurality of mini abutment members 12 are secured at selected locations in the jaw bone, depending on the size of the dental appliance to be secured, and caps 16 are secured at corresponding locations in the dental appliance. Male or retention members 15 are engaged in the respective caps, and the dental appliance can then be readily secured in the jaw by snap engaging the respective retention members over the opposing heads 20 of the abutment members.

The pitch or angle of the thread may be relatively steep and is in the range from around 9° to 17° in one embodiment. The spacing between adjacent threads is preferably at least 1 mm. It has been found that this is the minimum spacing required to ensure significant bone growth and osseointegration in the gaps between threads. The threads may project out around ½ mm from the surface of the shaft portion of the implant, and they are about ½ mm in height.

FIGS. 8 and 9 illustrate a modified implant 50 which may be used in place of the implant 12 in the anchor apparatus of FIGS. 1 to 7. Implant 50 has a modified threaded post 52. Other parts of the implant 50, particularly the head 20, are identical to corresponding parts in FIGS. 1 to 7, and like reference numbers have been used as appropriate. Threaded post 52 is shorter than post 14 of the previous embodiment and has a longer lead-in portion 54 which is unthreaded. Post 52 is slightly tapered along threaded portion 55 and has a flat end 56.

Figure 10:
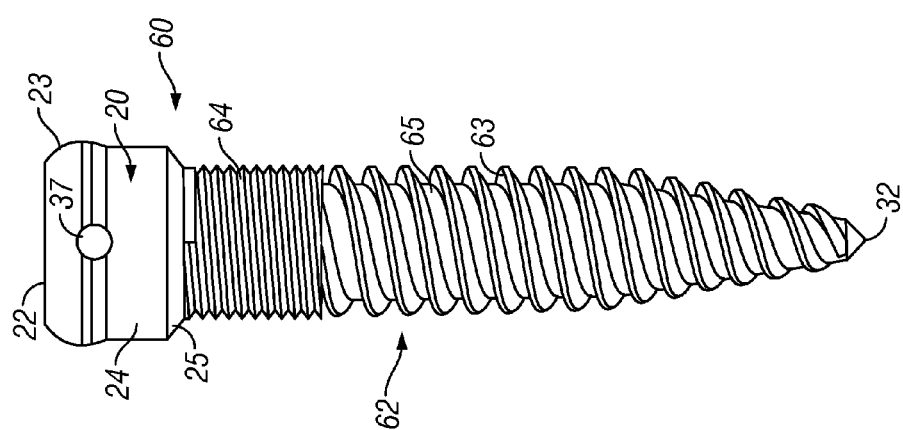
FIG. 10 is a side elevation view similar to FIG. 8 illustrating an implant with another modified threaded post for use in the apparatus of FIGS. 1 to 7.

FIG. 10 illustrates another modified implant 60 which may replace implant 12 of FIGS. 1 to 7. Implant 60 also has an abutment head 20 substantially identical to that of implant 12, but has a modified threaded shaft 62 which has no unthreaded lead in portion, and instead has micro-threads 64 in an upper portion of the shaft, followed by a double lead thread 63 along the lower portion 65 of the shaft with two threads offset by 180 degrees. Double lead threads will screw in twice as fast as a single lead thread. Bone grows into micro-threads faster and more effectively than larger threads, so this arrangement helps to anchor the implant and resists loosening.

Figure 12:
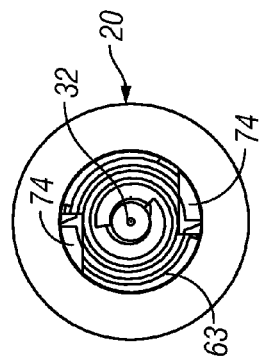
FIG. 12 is bottom plan view of the modified implant of FIG. 11, on a smaller scale than FIG. 11.
Figure 11:
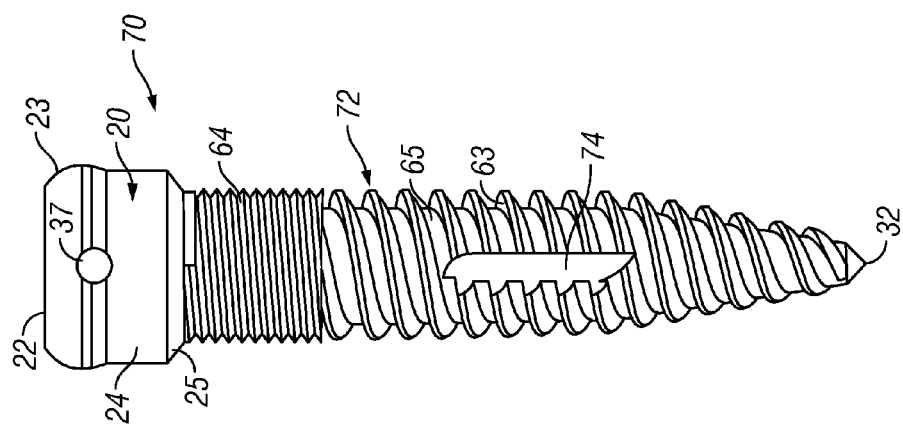
FIG. 11 is a side elevation view of another modified implant with a modified threaded post.

FIGS. 11 and 12 illustrate a modified implant 70 which has similar threads in the threaded shaft 72 to implant 60, and like reference numbers are used as appropriate. However, the threaded shaft 72 also has two diametrically opposed, axially extending flats 74 for self-tapping purposes. The flats also help to resist unthreading of the implant after implantation. Implant 70 is otherwise identical to implant 60, and like references numbers are used for like parts as appropriate. FIGS. 13 and 14 illustrate implant 70 together with the retention member 15 and cap 16 of FIGS. 1 to 7.

FIGS. 15 to 19 illustrate a dental anchor apparatus 80 according to another embodiment comprising a one-piece implant 82, a retention member 84, and a cap 85 designed to be secured in a recess or indent provided in a dental appliance such as a denture, partial denture, or the like. Implant 82 is similar to the implant of FIGS. 1 to 7 in some respects, and like reference numbers are used for like parts as appropriate, but has a shorter abutment head 86 and an integral threaded post or shaft 14 which is similar or identical to shaft 14 of FIGS. 1 to 7 apart from dimensional variations. The retention member 84 and cap 85 are also similar to retention member 15 and cap 16 of the first embodiment, and like reference numbers are used for like parts as appropriate. However, these parts are shorter in length than the corresponding parts of anchor apparatus 10, so that the overall height of the apparatus is reduced. Implant 82 is of relatively strong material such as coated titanium or other standard materials generally used for dental anchors or abutments, and the threaded post 14 is designed for direct engagement in a prepared bore in endosseous bone 100, in the same manner as indicated in FIG. 3 for the first embodiment.

Figure 16:
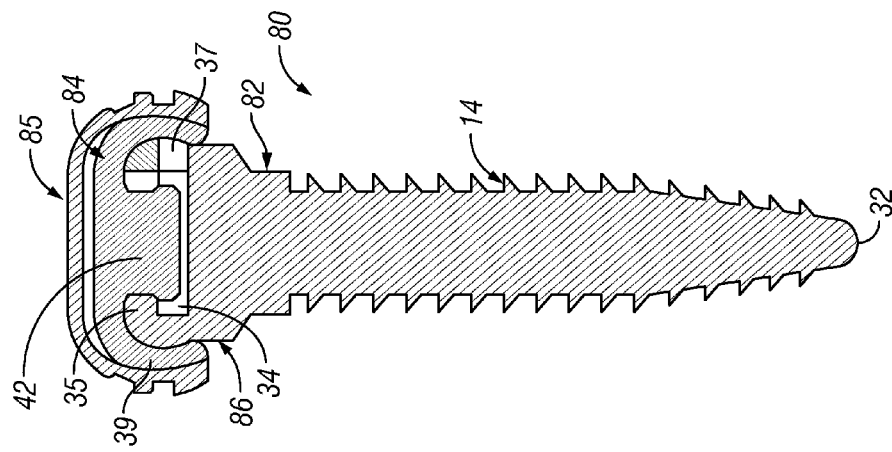
FIG. 16 is a cross-sectional view of the dental anchor apparatus of FIG. 15 with the parts assembled.
Figure 15:
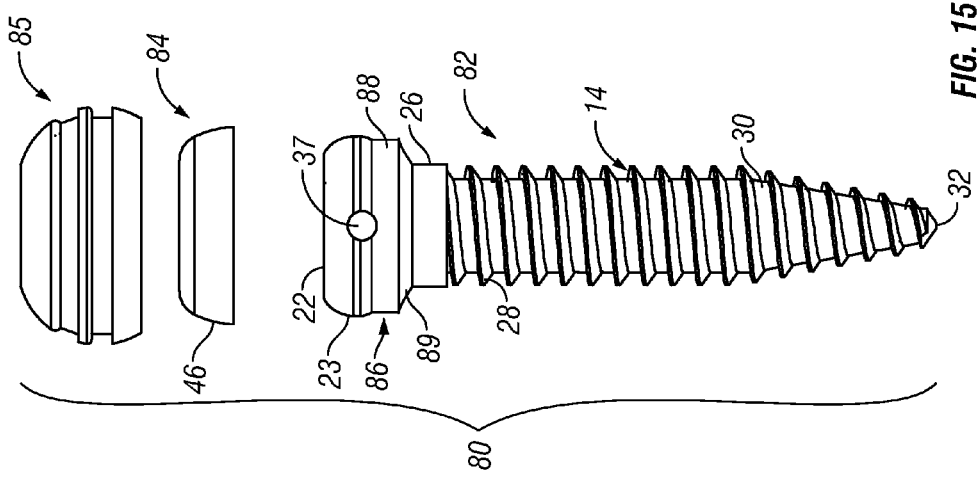
FIG. 15 is an exploded side elevation view of another embodiment of an anchor apparatus.

As in the first embodiment, abutment head 86 has a generally flat first end 22, and an outer curved or bulbous locating portion 23 extending from first end. A shortened cylindrical portion 88 extends from the end of locating portion 23, and an inwardly tapered rim portion 89 extends from cylindrical portion 88 up to the non-threaded end portion 26 of threaded post or shaft 14. FIG. 16 illustrates the parts of FIG. 15 assembled together. As illustrated in FIG. 16, retention member 84 is in hinging, snap engagement in cap 85 and is releasably snap engaged over the locating portion 23 of head 86. The threaded post may be coated by any suitable coating material prior to installation, as is known in the field of endosseous implants.

Figure 19:
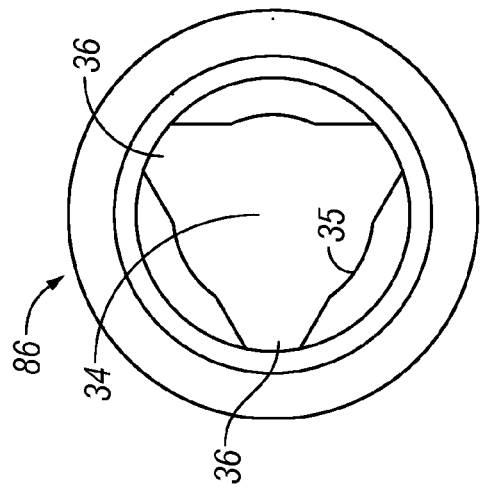
FIG. 19 is a top plan view of the implant of FIG. 18.
Figure 18:
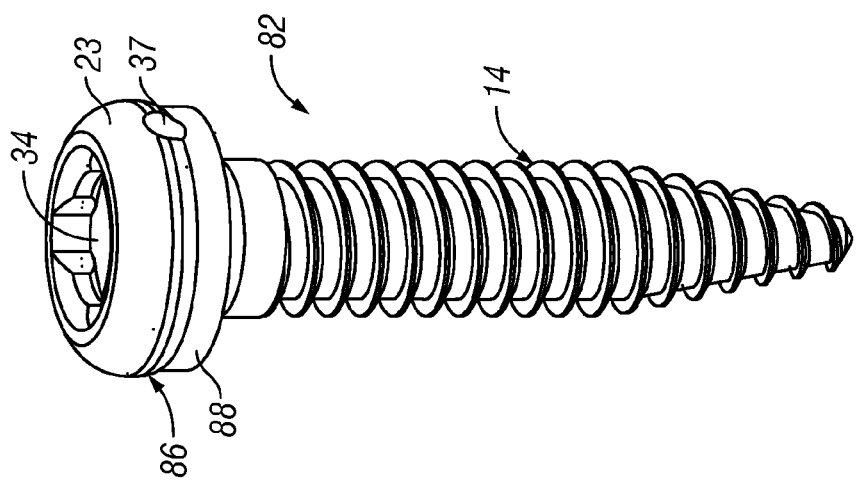
FIG. 18 is a perspective view of the implant of the apparatus of FIGS. 15 and 16.

As illustrated in FIGS. 16 and 18, and as in the previous embodiments, the head 86 of implant 82 has a socket 34 extending from flat end face 22 through part of the length of the head, and has an inwardly extending rounded rim 35 at the outer end of the socket. Rim 35 has cut-outs 36, as seen in FIGS. 18 and 19, for receiving the end of a suitable tool for securing the threaded post in a prepared bore in a patient's jaw bone. One or more weep holes 37 are provided through the wall of the socket to allow saliva to escape from the socket.

Figure 17:
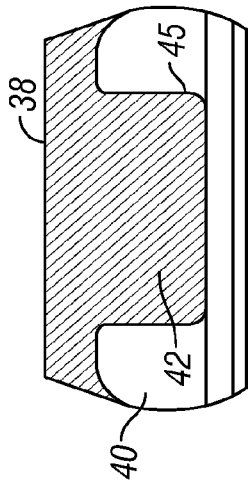
FIG. 17 is an enlarged sectional view of part of the retention member of the apparatus of FIGS. 15 and 16.

As illustrated in FIGS. 16 and 17, the retention member 84 is of similar cup-like shape to the previous embodiments, but shorter in length, with a generally flat first end 38, an outer skirt 39 extending from first end 38 defining an internal cavity 40 for engagement over the head 20, and a retention pin or post 42 extending from end 38 inside the cavity for engagement in socket 34, as seen in FIGS. 16 and 17. Retention member 84 is made of a material having some resilience, such as nylon, plastic, rubber, or rubber-like material. Retention member 84 may be similar to the retention or male elements as described in U.S. Pat. Nos. 6,030,219 and 6,299,447 of Zuest et al., the contents of which are incorporated herein by reference. As in the previous embodiments, the skirt 39 has a concave inner surface or locating portion 44 designed for snap engagement over the outer locating portion 23 of head 86. The retention pin or post 42 has an enlarged end portion 45 (FIG. 17) of slightly larger diameter than the remainder of the post, and slightly smaller diameter than the inner diameter of socket rim 35, with the rim 35 and end portion 45 comprising inner snap engaging formations. As the skirt 39 engages over outer locating portion 23 of the head, the end of post 42 is compressed slightly as it is forced through the opening defined by socket rim 35, and then expands so that it is releasably retained in the socket. Similarly, the outer end of skirt 38 is expanded as it is forced over the bulbous or rounded surface of locating portion 23, then snaps back to engage the end of locating portion 23. Thus, the locating portion 23 and inner concave surface of skirt 38 comprise a second set of snap engaging formations between the retention member 84 and the head 86 of implant 82.

The outer surface 46 of the retention member 84 is convex or rounded for snap-fit, swiveling engagement in a cavity 48 of corresponding shape in the cap 85, as in the previous embodiments, and as illustrated in FIG. 16. The swivel joint formed between the retention member and cap is similar or identical to that described in U.S. Pat. Nos. 6,030,219 and 6,299,447 referenced above. The pivoting of the nylon or plastic resilient retention or male member 84 in the metal denture cap 85 allows minor corrections for non parallel abutments as well as providing a longer lasting, resilient connection.

FIG. 20 illustrates a modified implant 95 which may be used in place of the implant 82 in the anchor apparatus of FIGS. 15 to 19. Implant 95 has an identical abutment head 86 to implant 82, but the threaded post 14 is replaced by a modified threaded post 62 which is identical to the threaded post illustrated and described above in connection with FIG. 10, and like reference numbers are used for like parts as appropriate. FIG. 21 illustrates another modified implant 96 which may replace implant 82 of FIGS. 15 to 19. Implant 96 also has a head 86 substantially identical to that of implant 82, but has a modified threaded shaft 72 identical to the shaft of the implant 70 of FIGS. 11 to 14, and like reference numbers are used for like parts as appropriate.

Figure 24:
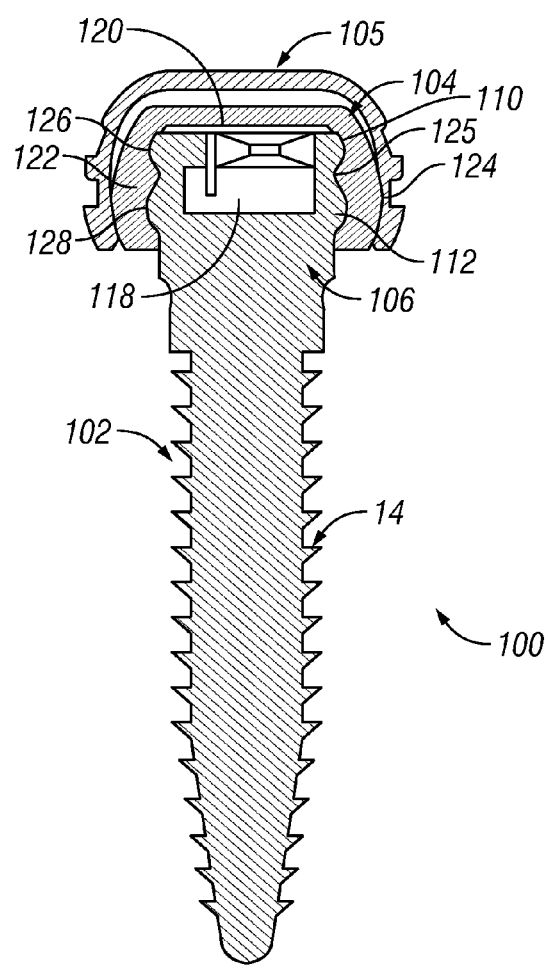
FIG. 24 is a cross-sectional view on the lines 23-23 of FIG. 23.

FIGS. 22 to 24 illustrate a dental anchor apparatus 100 according to another embodiment comprising a one-piece endosseous implant 102, a retention member 104, and a cap 105 designed to be secured in a recess or indent provided in a dental appliance such as a denture, partial denture, or the like. Implant 102 has a modified abutment head 106 and an integral threaded post or shaft 14 which is similar to the threaded shaft of the implant of FIGS. 1 to 7, and like reference numbers are used for like parts as appropriate. As in the previous embodiments, implant 102 is of relatively strong material such as coated titanium or other standard materials generally used for dental anchors or abutments, and the threaded post 14 is designed for direct engagement in a prepared bore in endosseous bone 100, in the same manner as indicated in FIG. 3 for the first embodiment. The threaded post may be coated by any suitable coating material prior to installation, as is known in the field of endosseous implants.

Retention member 104 is of a material having some resilience, such as nylon or plastic material, as in the previous embodiments. Retention member 104 may be similar or identical to the retention or female member described in U.S. Pat. No. 6,981,871 of Mullaly et al., the contents of which are incorporated herein by reference, while head 106 of the implant 102 is similar to the head of the device described in U.S. Pat. No. 6,981,871 to provide a similar outer snap engagement mechanism.

Head 106 has a first end 108, and an outer locating surface projecting away from the first end which has at least two axially spaced retention or snap engagement portions 110, 112 which comprise annular retention ribs separated by an annular groove 114. In the illustrated embodiment, the first rib or retention portion 110 is of smaller diameter than the second rib or retention portion 112, although they may be of the same diameter in other embodiments. A cylindrical portion 115 extends from rib 112 and terminates in a tapered portion 116 transitioning to the non-threaded end portion 26 of threaded post 14. As in the previous embodiments, a socket 118 extends inwardly from the end 108 of the head, with cut outs around the rim for receiving a tool used for screwing the post 14 into a prepared bore in endosseous bone. However, in this case, the retention member 104 does not have any post which is in snap engagement in bore 118, since an external snap engagement only is provided, as explained in more detail below. In alternative embodiments, an inner snap engagement may also be provided between retention member 104 and the head of implant 102 in a similar manner to the previous embodiments. One or more weep holes (not illustrated) may be provided through the wall of the socket 118 to allow saliva to escape from the socket.

As illustrated in FIG. 24, retention member 104 is of generally cup-like shape having a first end 120 and a skirt 122 projecting from the first end for snap engagement over the locating or retention portions of head 106. As noted above, retention member 104 is similar or identical to the retention member described in U.S. Pat. No. 6,981,871 referenced above. The outer surface 124 of skirt 122 is arcuate and designed for swivel engagement in cap 105, as seen in FIG. 24.

The inner surface of skirt 122 has a projecting annular rib 125 separating the cavity into first and second annular indented regions or rounded grooves 126, 128 for snap engagement over ribs 110, 112. As illustrated in FIG. 24, when the parts are assembled together, retention member 104 is in hinging, snap engagement in cap 105 and is releasably snap engaged over the locating portions of head 106. The swivel joint formed between the retention member and cap is similar or identical to that described in U.S. Pat. Nos. 6,030, 219, 6,299,447, and 6,981,871 referenced above. The pivoting of the nylon or plastic resilient retention member 104 in the metal denture cap 105 allows minor corrections for non parallel abutments as well as providing a longer lasting, resilient connection. At the same time, the retention member is held securely in the cap as the patient removes and replaces the dental appliance.

Figure 25:
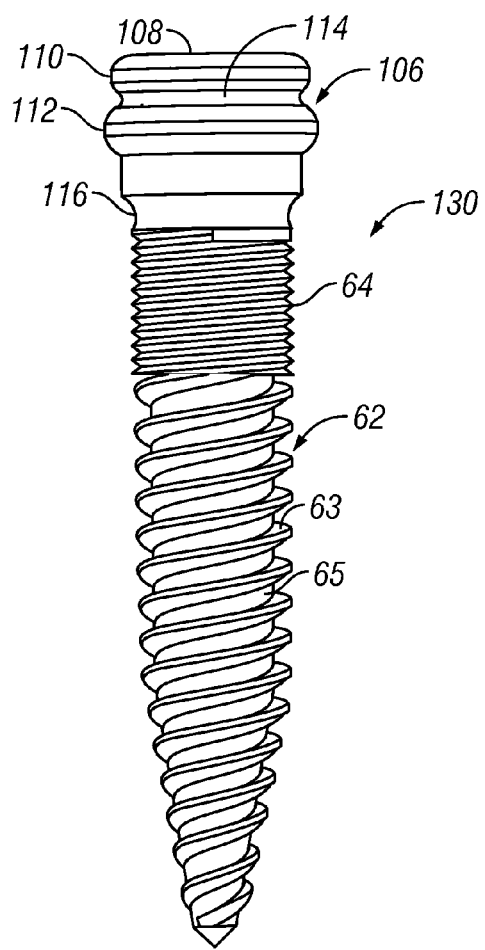
FIG. 25 is a side elevation view of an endosseous implant similar to the implant in the apparatus of FIGS. 22 to 24 but with a modified threaded post.
Figure 26:
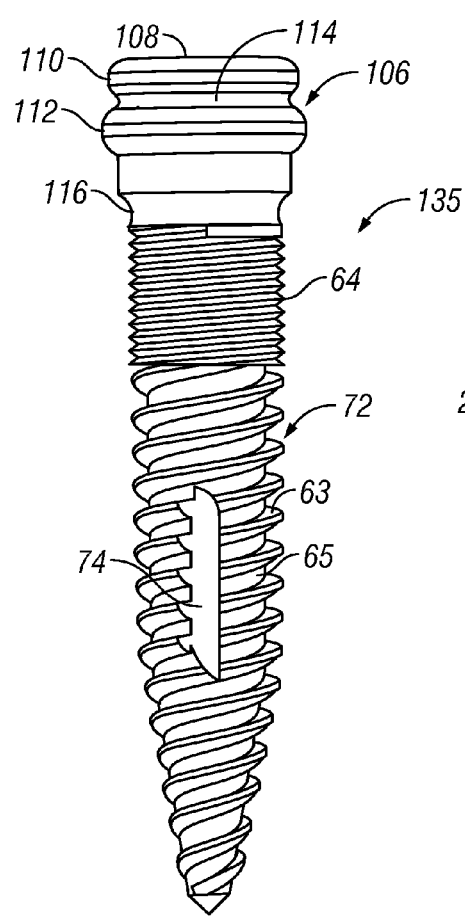
FIG. 26 is a side elevation view of an implant similar to the implant of FIG. 25 but with a modified threaded post.

FIG. 25 illustrates a modified implant 130 which may be used in place of the implant 102 in the anchor apparatus of FIGS. 22 to 24. Implant 130 has an identical abutment head 106 to implant 102, but the threaded post 14 is replaced by a modified threaded post 62 which is identical to the threaded post illustrated and described above in connection with FIG. 10, and like reference numbers are used for like parts as appropriate. FIG. 26 illustrates another modified implant 135 which may replace implant 102 of FIGS. 22 to 24. Implant 135 also has a head 106 substantially identical to that of implant 102, but has a modified threaded shaft 72 identical to the shaft of the implant 70 of FIGS. 11 to 14, and like reference numbers are used for like parts as appropriate.

In each of the above embodiments, an implant with an integral abutment head designed for snap engagement with a retention member retained in a cap in a dental prosthesis can be directly implanted into a prepared bore in the jawbone, expediting delivery of a finished denture, partial denture, or other dental prosthesis to a patient. Two or more such implants are placed at selected locations in a patient's mouth, depending on the size and location of the dental prosthesis to be installed. Bores are first prepared at suitable locations in the jaw bone, and the threaded shafts of the selected implants are threaded into the bores. As noted above, the shafts or posts may first be treated with suitable coating and/or adhesive materials. Once installed, the locating portions of the integral abutment heads project above the bone and the gum level for snap engagement in opposing retention members which are in swivel engagement with caps secured in the dental appliance. The resilient nylon or plastic retention members remain in static engagement with the integral heads of the implant when the appliance is in place, while the metal caps have a full range of rotational or swivel movement over the retention members while the dental appliance is in use, and can compensate for any misalignment between implants. At the same time, the wearer can readily remove the appliance by snapping the retention members off the heads of the implants as necessary for cleaning purposes, and can easily replace the appliance by urging the retention members onto the heads of the aligned implants until they snap into place.

Figure 27:
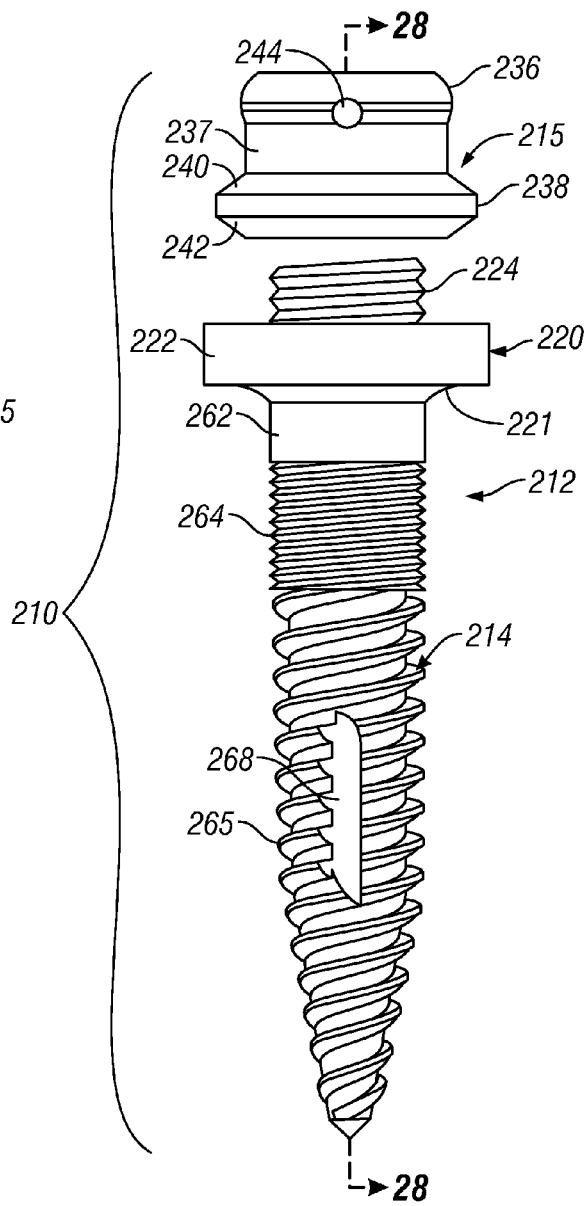
FIG. 27 is an exploded side elevation view of a two part mini implant according to another embodiment, with the parts of the implant separated.
Figure 28:
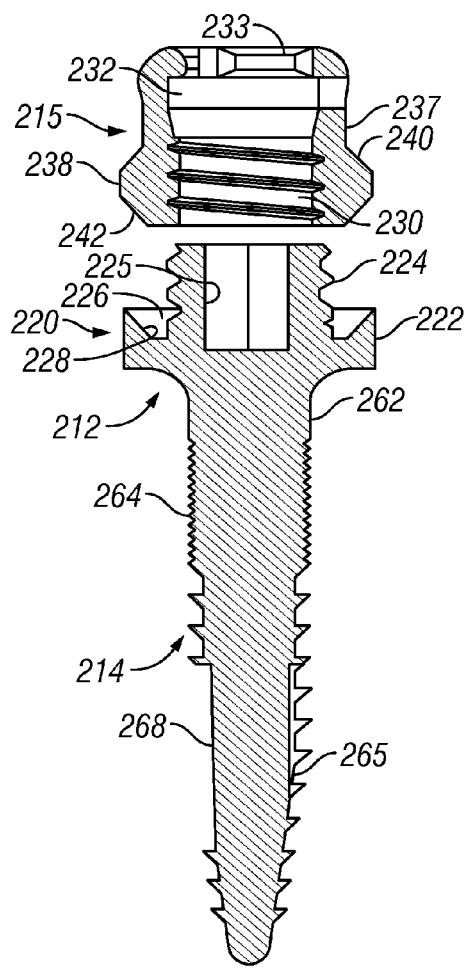
FIG. 28 is a longitudinal cross sectional view of the two part mini implant of FIG. 27 on the lines 28-28 of FIG. 27.
Figure 31:
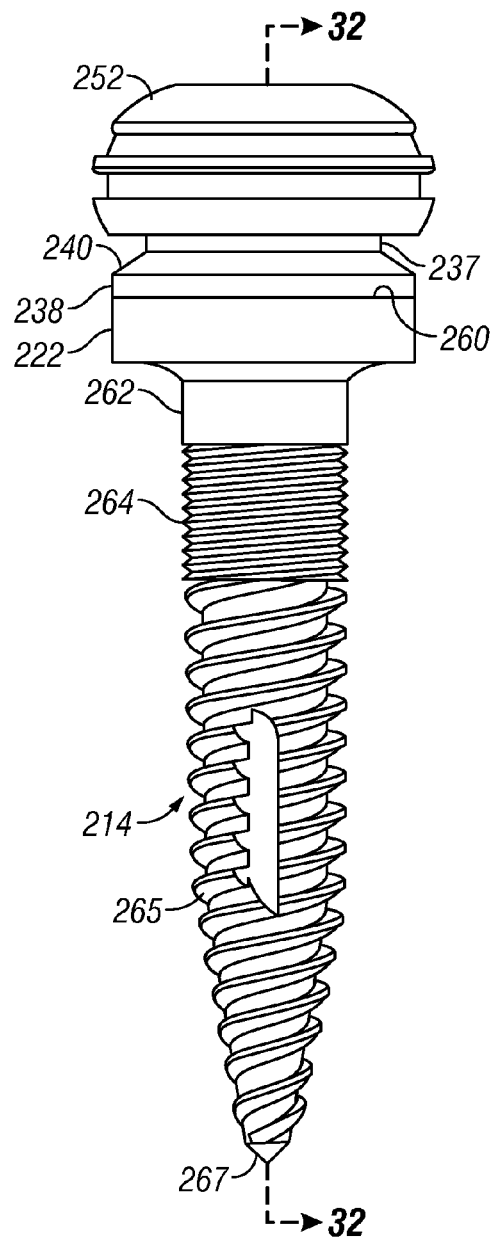
FIG. 31 is a side elevation view illustrating the two parts of the mini implant or attachment member of FIGS. 27 to 30 secured together and in use and in releasable snap engagement with a male or retention member which is in swivel engagement in a cap positioned in a denture or dental appliance.
Figure 32:
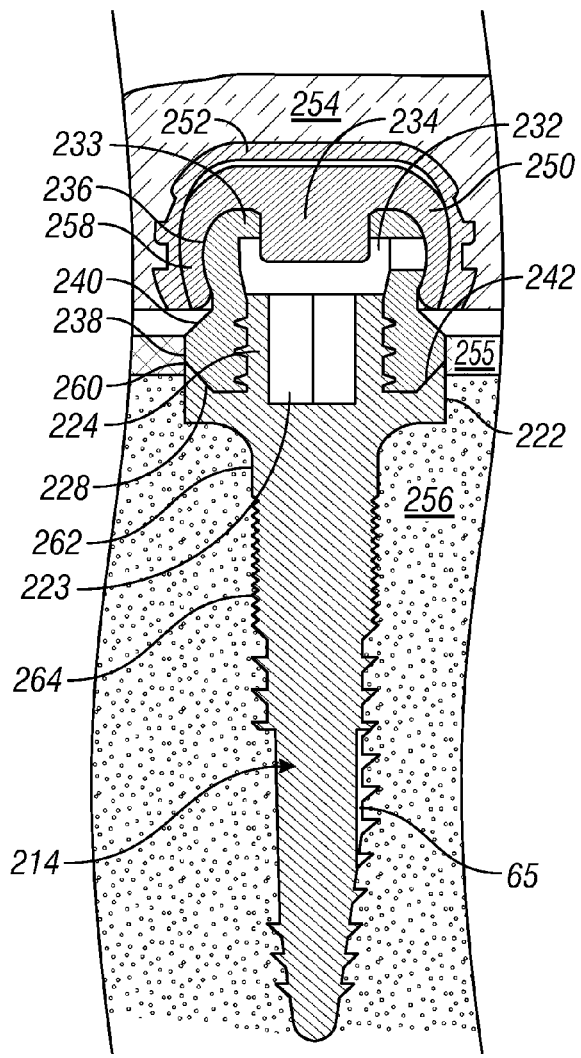
FIG. 32 is a longitudinal cross sectional view of the dental anchor apparatus of FIG. 31 on the lines 32-32 of FIG. 31, schematically indicating the endosseous hard bone level, soft tissue area, and the area above the surrounding tissue when the assembly is in use.

FIGS. 27 to 32 illustrate a dental attachment or anchor apparatus 200 according to another embodiment comprising an implant 210, a retention member 250, and a cap 252 which is similar to cap 16 of the previous embodiments. The implant 210 is shown separate from the other parts in FIGS. 27 to 30, while all of the parts are shown assembled together in FIGS. 31 and 32, as described in more detail below. In this embodiment, the one-piece implant of the previous embodiments is replaced with a two-piece implant 210 comprising a main body 212 with a first end portion 220 at a first end of the body and an integral threaded post or shaft 214 extending from the end portion 220, and a separate abutment head or member 215 which is removably securable to the main body. FIGS. 27 and 28 illustrate the two parts of the implant 210 separated from one another, while FIGS. 31 and 32 illustrate the abutment head 215 secured to the first end portion 220 of the main body, along with retention member 250 snap engaged with outer and inner locating portions of the abutment head, and in swivel engagement in a cap 252 designed to be secured in an indent in a dental appliance 254 such as an overdenture, a partial denture, or the like. The two piece implant 210 is of relatively strong material such as coated titanium or other standard materials generally used for dental anchors or abutments, for example titanium with a coating layer of titanium nitride on the attachment or locator surfaces of abutment member 215. In one embodiment, the threaded post 214 is designed for direct engagement in a prepared bore in endosseous bone 256, as indicated in FIG. 32.

Figure 29:
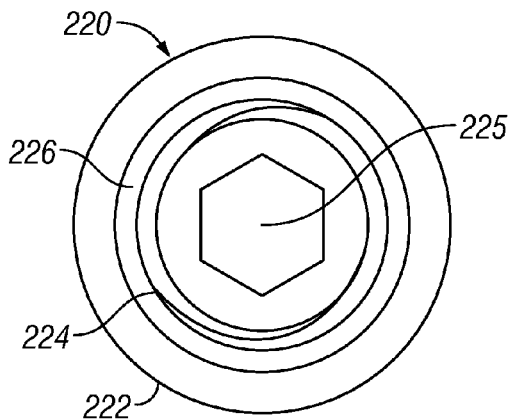
FIG. 29 is a top plan view of the main body of the implant of FIGS. 27 and 28, illustrating the internal hex.
Figure 30:
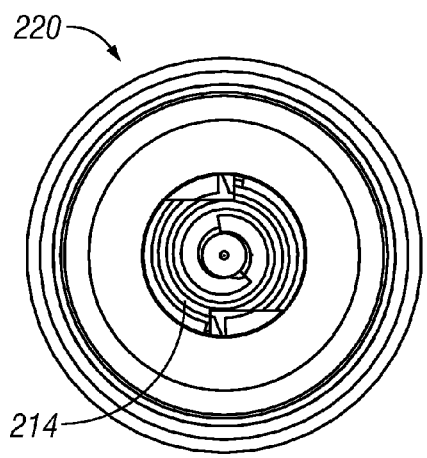
FIG. 30 is a bottom plan view of the main body of the implant of FIGS. 27 and 28.

In the embodiment of FIGS. 27 to 32, the first end portion 220 of the main body 212 has an external thread which connects the two parts of the implant together. The first end portion 220 of body 212 comprises annular cuff portion 222 and an externally threaded projection or boss 224 extending from one end of cuff portion 222. Threaded stem or post 214 extends from the other end of cuff portion 222, which has a curved, tapered lead-in 221 to the reduced diameter post 214. As best illustrated in FIGS. 28 and 29, a hexagonal, tool-receiving bore 225 extends inwardly from the upper end of threaded projection 224. An annular seat or beveled cup portion 226 with a recessed, inwardly tapered bevel or rim 228 surrounds projection 224 at the upper end of cuff portion 222, as best illustrated in FIG. 28.

Figure 28A:
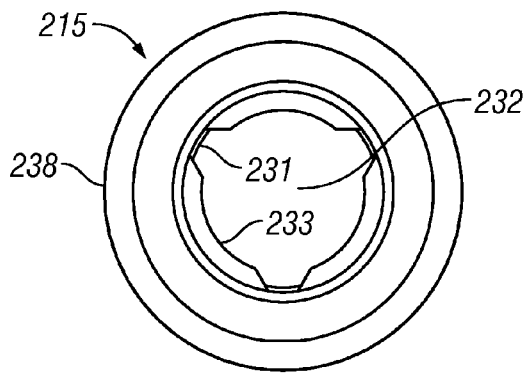
FIG. 28A is a top plan view of the abutment head of the two part implant of FIGS. 27 and 28.

Abutment head or member 215 has a through bore with a threaded lower end portion 230 which is designed for releasable threaded engagement with the external threads on projection or boss 224 at the upper end of the main body 212. The upper or first end of the through bore comprises a socket 232 with an inwardly projecting, bulbous peripheral rim 233 for releasable snap engagement with the end of a post 234 of retention member 250 located in a denture or dental appliance, as illustrated in FIGS. 31 and 32 and described in more detail below. The peripheral rim 233 has three indents 231 in a triangular pattern for engaging a removal tool, as illustrated in FIG. 28A and as described in more detail below in connection with FIGS. 33, 34, and 34A. The abutment head has a first, convex or bulbous locating portion 236 extending from the flat upper or first end of the member, a cylindrical waist portion 237 extending from end portion 235, an outer annular rim 238 connected to the waist portion by outwardly tapered portion 240, and an inwardly tapered or bevel portion 242 extending from the waist portion to the flat lower end of the member 215. Annular rim 238 forms part of the cuff of the implant when the parts are secured together, as seen in FIGS. 31 and 32. One or more weep holes 244 may be provided through the wall of the socket, as seen in FIG. 27, to allow saliva to escape from the socket. The taper and dimensions of lower bevel portion 242 match those of the inner bevel 228 at the upper end of the main body.

FIGS. 31 and 32 illustrates the two parts of FIGS. 27 and 28 assembled together, with the abutment head 215 in threaded engagement over the threaded projection 224 and the lower bevel 242 engaging inner bevel 228 of seat 226 in the upper or first end portion of the main body. The seating of the lower end of the abutment head 215 in the upper beveled cup portion 226 of the main body, along with the engagement of the beveled lower end face 242 against the corresponding beveled rim 228 of the cup portion 226, helps to reduce lateral stress on the thread connecting the two parts.

In FIGS. 31 and 32, the two part mini implant is shown in use and in releasable snap engagement with a cap male or retention member 250 which is in swivel engagement in a cap 252 secured in a recess in a denture or dental appliance 254, part of which is schematically illustrated in FIG. 32. FIG. 32 also schematically illustrates the tissue or gum 255 surrounding the implant and hard or endosseous bone 256 in which threaded post 214 is embedded, and the approximate location of the attachment parts relative to the bone and tissue level. The outer separation line 260 between the two parts of the implant 210 is located along the height of the cuff region and slightly below the tissue level when the implant is installed, as seen in FIGS. 31 and 32.

In FIGS. 31 and 32, the retention member 250 is in hinging, snap engagement in cap 252 and releasably snap engaged over the outer locating surface portion 236 of abutment head 215. At the same time, post or shaft 234 is in snap engagement in socket 232. FIG. 32 schematically illustrates the operative condition of the parts, with cap 252 installed in a suitable cavity in a dental appliance or prosthesis 254, and the threaded post 214 in threaded engagement in a prepared bore in jaw bone 256. The threaded post may be coated by any suitable coating material prior to installation, as is known in the field of endosseous implants.

Retention member 250 may be similar to the retention or male elements as described in U.S. Pat. Nos. 6,030,219 and 6,299,447 of Zuest et al., the contents of which are incorporated herein by reference, and may be a male or retention member as sold by Zest Anchors of Escondido, Calif. under the name Locator®. In alternative embodiments, the abutment member may be designed for releasable snap engagement with other types of male or retention members as used in dentures, while attaching to the main body of the implant in the same way as indicated in the drawings. The retention member 250 of FIGS. 31 and 32 has a skirt 258 with a concave inner surface or locating portion designed for snap engagement over the outer locating portion 236 of the abutment member. The retention pin or post 234 has an enlarged end portion of slightly larger diameter than the remainder of the post, and slightly smaller diameter than the inner diameter of socket rim 233, with the rim 233 and the end portion of post 234 comprising snap engaging formations. As the skirt engages over outer locating portion 232 of the head, the end of post 234 is compressed slightly as it is forced through the opening defined by socket rim 233, and then expands so that it is releasably retained in the socket. Similarly, the outer end of skirt 258 is expanded as it is forced over the bulbous or rounded surface of locating portion 232, then snaps back to engage over the end of locating portion 232 against the reduced diameter waist portion 237, as seen in FIG. 32. The outer surface of the retention member 250 is convex or rounded for snap-fit, swiveling engagement in a cavity of corresponding shape in the cap 252, as illustrated in FIG. 32, with the small gap between the opposing inner ends of cap 252 and retention member 250 allowing a small degree of swivel. The swivel joint formed between the retention member and cap is similar or identical to that described in U.S. Pat. Nos. 6,030,219 and 6,299,447 referenced above. The pivoting of the nylon or plastic resilient retention or male member 250 in the metal denture cap 252 allows minor corrections for non parallel abutments as well as providing a longer lasting, resilient connection.

The two piece implant may be made in a range of different sizes for selection by a dental surgeon or dentist based on the size of a patient's jaw and the available tissue and bone depth and thickness. The two piece implant 210 may be provided in a similar size range to so-called mini abutment members or mini implants. In one embodiment, abutment members 215 are provided in a range of diameters from around 1.5 mm. to 4.0 mm., while the length of the threaded post 214 may be in the range from around 6 mm. to 21 mm. A plurality of two piece implants are secured at selected locations in the jaw bone, depending on the size of the dental appliance to be secured, and caps 252 are secured at corresponding locations in the dental appliance. Male or retention members 250 are engaged in the respective caps, and the dental appliance can then be readily secured in the jaw by snap engaging the respective retention members over the opposing ends or locating portions of the abutment heads 215.

In one embodiment, the threads on the shaft or post 214 of the main body may be designed to allow bone growth and osseointegration. In the illustrated embodiment, the threads are designed for bone growth and the pitch or angle of the thread on the shaft or post 214 of the main body is relatively steep and may be in the range from around 9° to 17°. The spacing between adjacent threads may be at least 1 mm. It has been found that this is the minimum spacing allowing significant bone growth and osseointegration in the gaps between threads. In one embodiment, the threads project out around ½ mm from the surface of the shaft portion of the implant, and are about ½ mm in height. The thread design may be similar or identical to that described above in connection with the one-piece implants of FIGS. 1 to 26. In the embodiment of FIGS. 27 to 32, the shaft has an unthreaded lead in portion 262 followed by a micro-threaded portion 264, and a double lead thread 265 along the lower portion of the shaft. Double lead threads will screw in twice as fast as a single lead thread. Bone grows into micro-threads faster and more effectively than larger threads, so this arrangement helps to anchor the implant and resists loosening. In the illustrated embodiment, the threaded portion of shaft 214 also has two diametrically opposed, axially extending flats 268 for self-tapping purposes. The flats also help to resist unthreading of the implant member after implantation. Other thread designs may be used in alternative embodiments. In the illustrated embodiment, shaft 214 is tapered along at least part of its length up to tip 267, but may be of uniform diameter in other embodiments. Alternative thread or other bone integration formations may be used in other embodiments.

Figure 33:
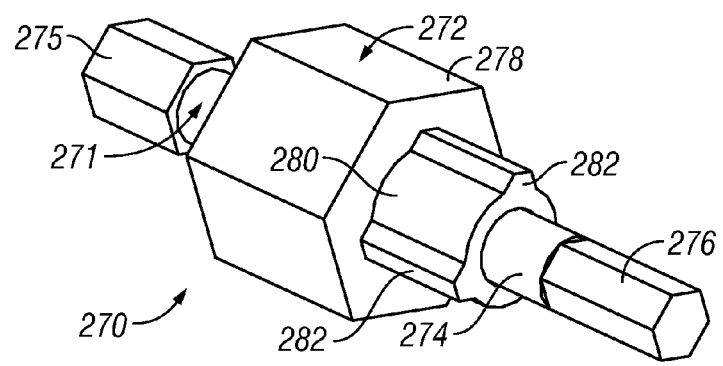
FIG. 33 is a perspective view of a driver or removal tool for separating the abutment head from the main body of the implant of FIGS. 27 to 32 when needed for repair or replacement purposes.
Figure 34:
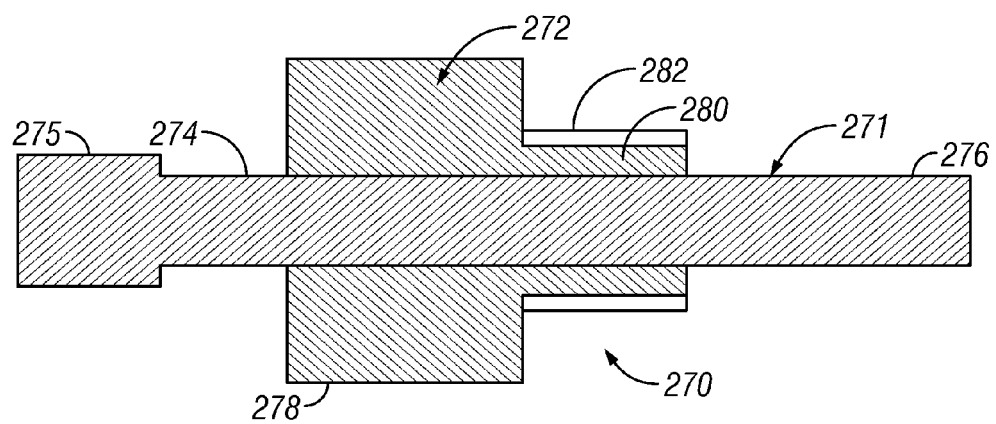
FIG. 34 is a longitudinal cross sectional view of the removal tool of FIG. 33.
Figure 34A:
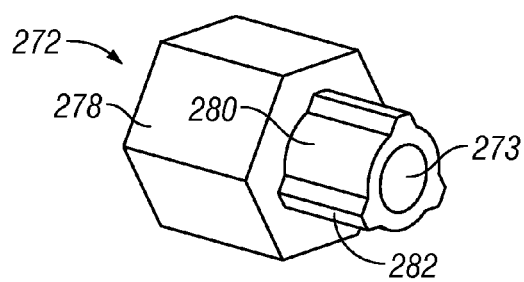
FIG. 34A is a perspective view of the triangle driver of the removal tool of FIGS. 33 and 34.
Figure 35:
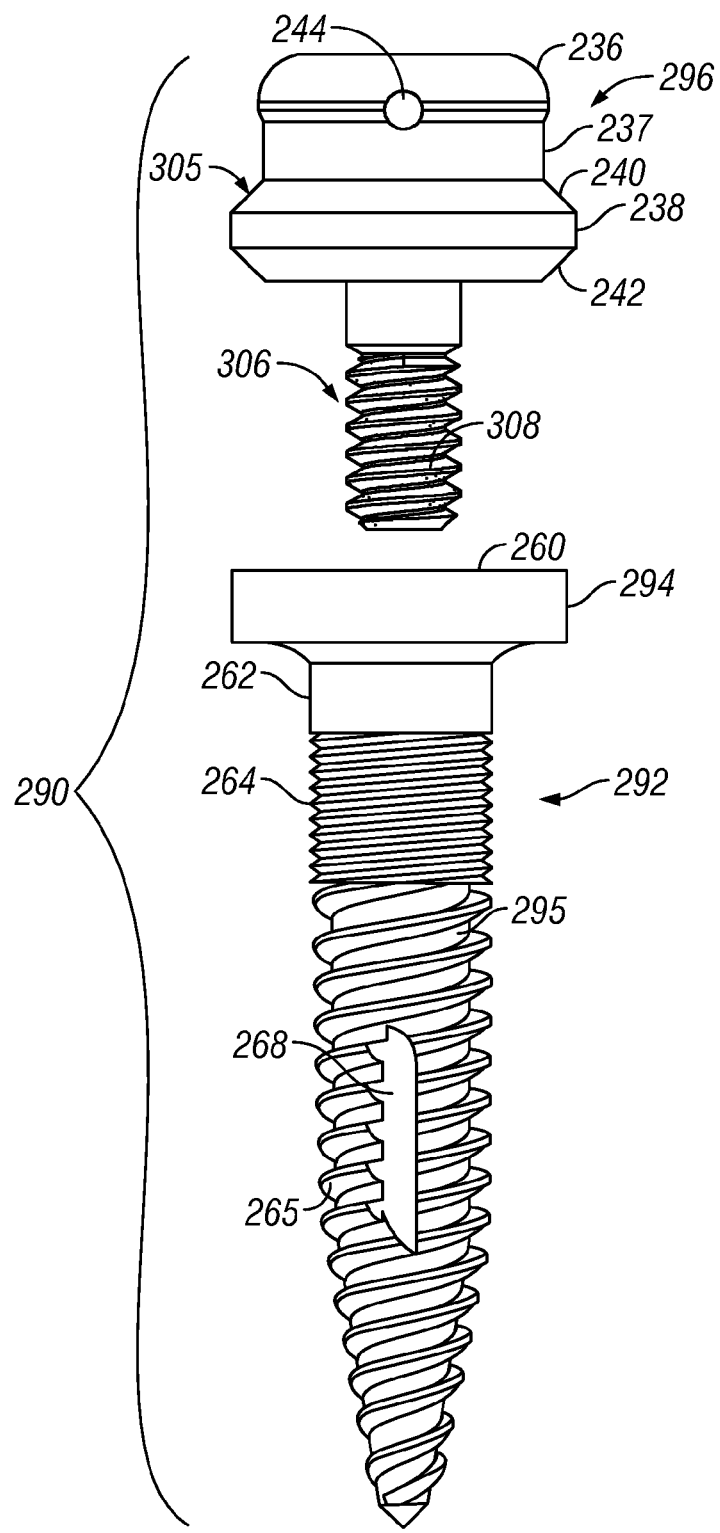
FIG. 35 is an exploded side elevation view of a two part mini implant according to another embodiment, with the parts of the implant separated.
Figure 36:
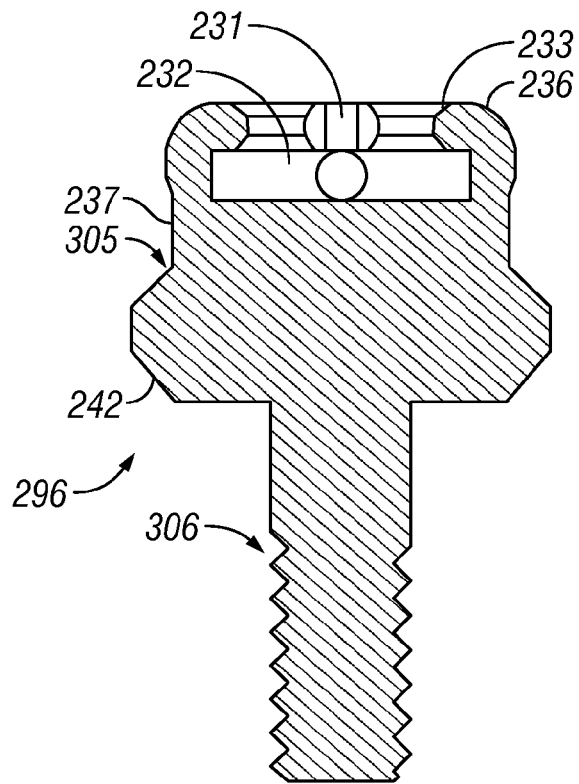
FIG. 36 is a longitudinal cross-sectional view of the abutment head of the mini implant of FIG. 35.
Figure 37:
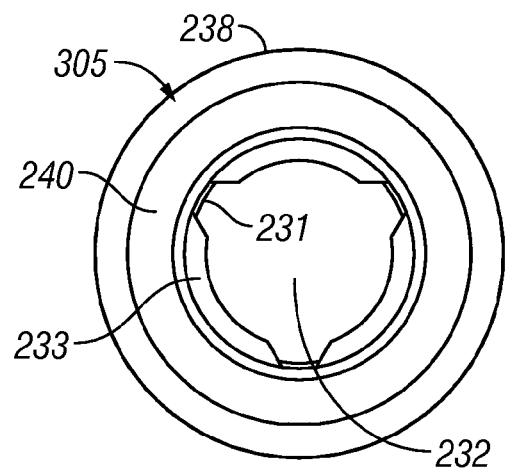
FIG. 37 is a top plan view of the abutment head of FIG. 36.

By making the mini implant in two pieces rather than one, the upper abutment head or member 215 can be replaced while leaving the main body of the implant in place in the jaw bone, which is an advantage over a one piece implant which would have to be completely removed and replaced or altered to continue proper usage when the attachment or locating surfaces become worn. In the embodiment of FIGS. 27 to 32, the abutment member 215 can be removed from the main body by the dentist by unscrewing it from the externally threaded boss or post 224 at the upper end of the main body 212 of the implant. FIGS. 33, 34 and 34A illustrate one embodiment of a removal tool 270 which may be used to remove the abutment member 215 from the main body 212 of the two piece implant if the retention or snap engagement surfaces become worn, requiring replacement of member 215. The removal tool has a central shaft 271 and a triangle driver or sleeve 272 rotatably mounted over a central region of the shaft, as seen in FIG. 34. Shaft 271 has a generally cylindrical central portion 274 on which the driver 272 rotates, a hexagonal wrench holding portion 275 at one end, and a smaller hexagonal portion 276 at the opposite end designed to engage in the hexagonal bore 225 at the upper end of the main body 212. Triangle driver 272 is illustrated separately in FIG. 34A and comprises a sleeve member having a central cylindrical through bore 273 rotatably engaged over central portion 274 of the shaft, a first, larger end portion or gripping portion 278 of hexagonal shape, and a drive portion 280 which has three spaced ears or ribs 282 arranged in triangle and designed to engage in the triangular arrangement of indents or notches 231 in the inner rim 233 of the socket 232 in abutment member 215.

In order to remove the abutment head 215, the lower hex portion 276 of the removal tool is engaged in the internal hex 225 of the main body of the implant to hold it in place and protect it from unthreading stress. The driver portion 280 of the triangle driver 272 is engaged in the socket 232 of the abutment head 215 with the ears or ribs 282 engaging in notches 231, and is then rotated to unthread the abutment member head 215 from threaded post or boss 224 while the lower hex portion 276 of the shaft holds the main body stationary. The lower hex portion 276 may also be used for threading the main body 212 into a prepared bore in the jaw bone on original installation of the implant.

FIGS. 35 to 38 illustrate a two piece mini implant 290 according to a second embodiment, in which the external threaded attachment to the main body of the implant is replaced with an internal threaded attachment. The mini implant 290 comprises a main body 292 with an enlarged first end portion 294 at a first end of the body and an integral threaded post or shaft 295 extending from the first end portion, and a separate abutment head 296 which is removably securable to the main body. The implant is of identical or similar materials to the previous embodiment. The external threaded arrangement of the shaft 295 is identical to the previous embodiment, and like reference numerals are used for like portions of the shaft as appropriate.

Figure 38:
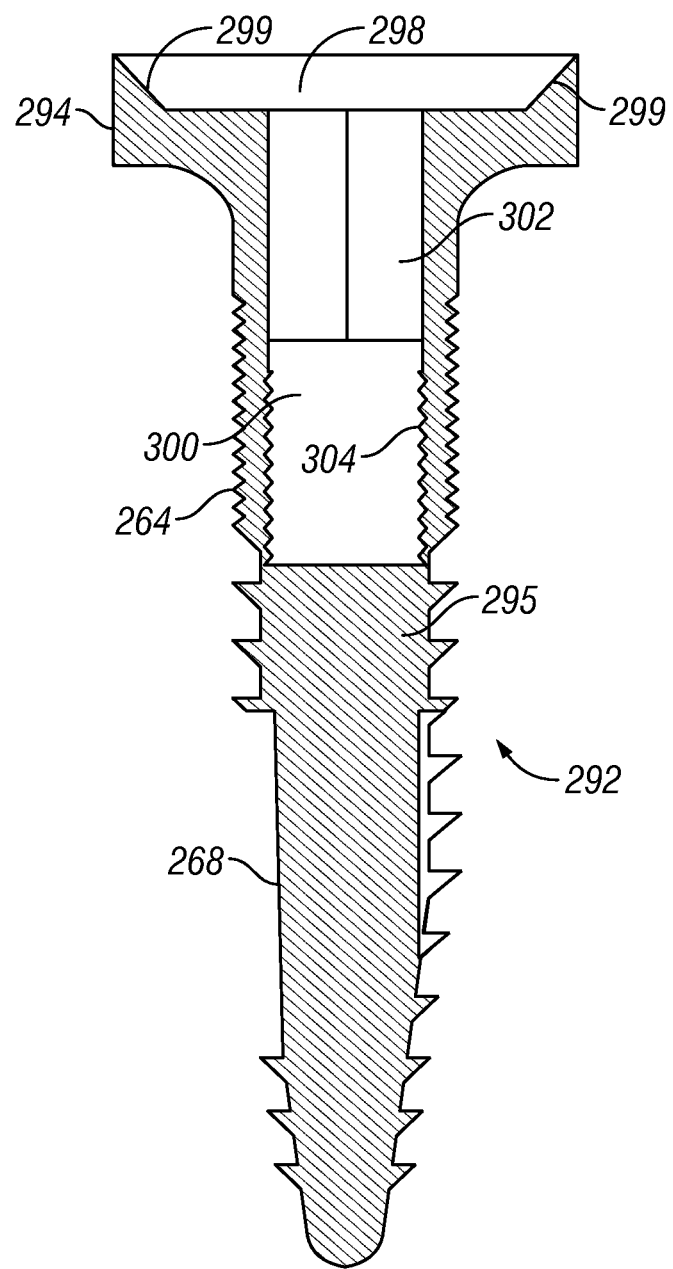
FIG. 38 is a longitudinal cross-sectional view of the internally threaded main body of the implant of FIG. 35.

The first end portion 294 comprises a cylindrical cuff portion similar to that of the previous embodiment, with a cup shaped seat 298 having a beveled outer rim 299 and a bore 300 extending from the seat into the shaft portion of the main body having a hex portion 302 at its upper end (see FIG. 38). Bore 300 is longer than in the previous embodiment and has a threaded inner end portion 304. The abutment head 296 has an end portion 305 of similar external shape to abutment head 215, with a similar upper end socket 232 to the previous embodiment, and like reference numbers have been used for like parts as appropriate. However, instead of a threaded bore as in the previous embodiment, the abutment head 296 of this embodiment has a shaft 306 which extends from portion 305 and has a threaded portion 308 for threaded engagement in the threaded inner end portion 304 of the bore in main body 292. Thus, in this embodiment, an internal thread connects the two parts of the mini implant. The abutment head 215 may be removed for replacement if needed by unthreading it from the main body, using a triangle driver similar to the triangle driver of tool 270 illustrated in FIG. 34A.

As in the previous embodiment, the lower beveled portion 242 of end portion 305 of abutment head 296 is seated in cup-shaped seat 298 at the upper end of the main body when the parts are secured together via the internal thread attachment, with the lower beveled face 242 of the abutment head engaging the beveled rim 299 of seat 298. This helps to reduce lateral stress on the smaller thread 308, 304 which connects the two parts.

Once installed in the jaw, the two piece implant 290 functions in exactly the same way as described above in connection with the previous embodiment, with a male or retention member 250 snap engaging over the upper end of head portion 305 with its post 234 in snap engagement in socket 232, as described above in connection with FIGS. 31 and 32. A plurality of two piece mini implants 290 can therefore be used to releasably attach a denture or dental appliance in a patient's mouth, using standard male or retention members in swivel engagement in appropriately placed caps 252 in the appliance.

Figure 39:
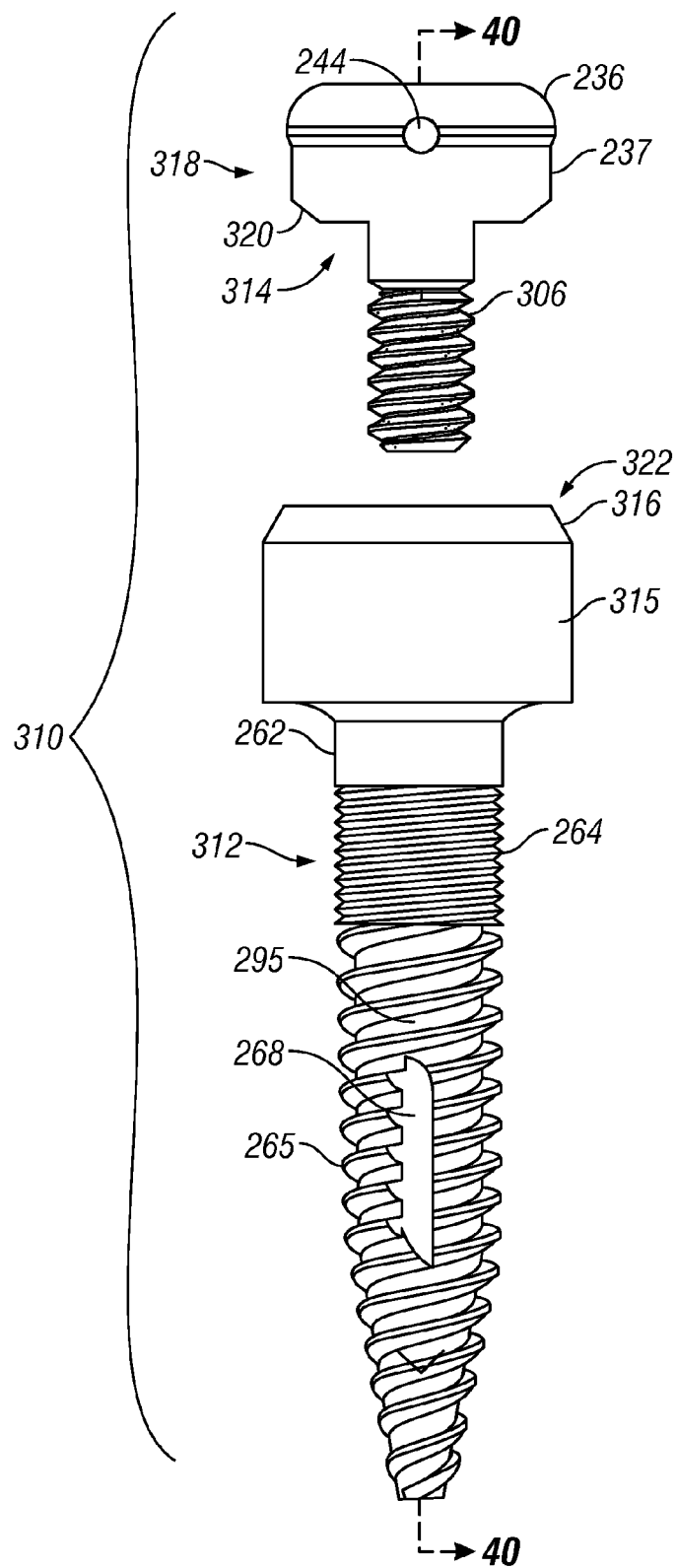
FIG. 39 is an exploded side elevation view of a modified two part mini implant according to another embodiment, which is similar to the internal thread attachment implant of FIGS. 33 to 38 but with the line of separation between the two parts at a different location.
Figure 40:
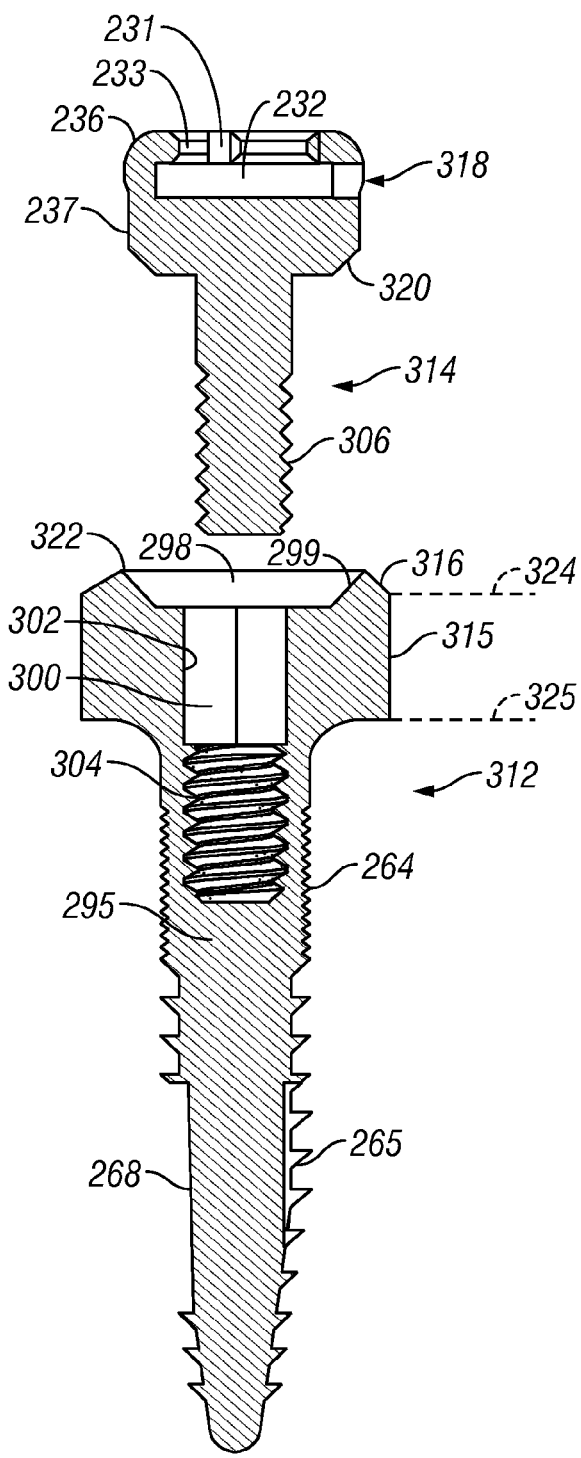
FIG. 40 is a vertical cross-sectional view on the lines 40-40 of FIG. 39.
Figure 41:
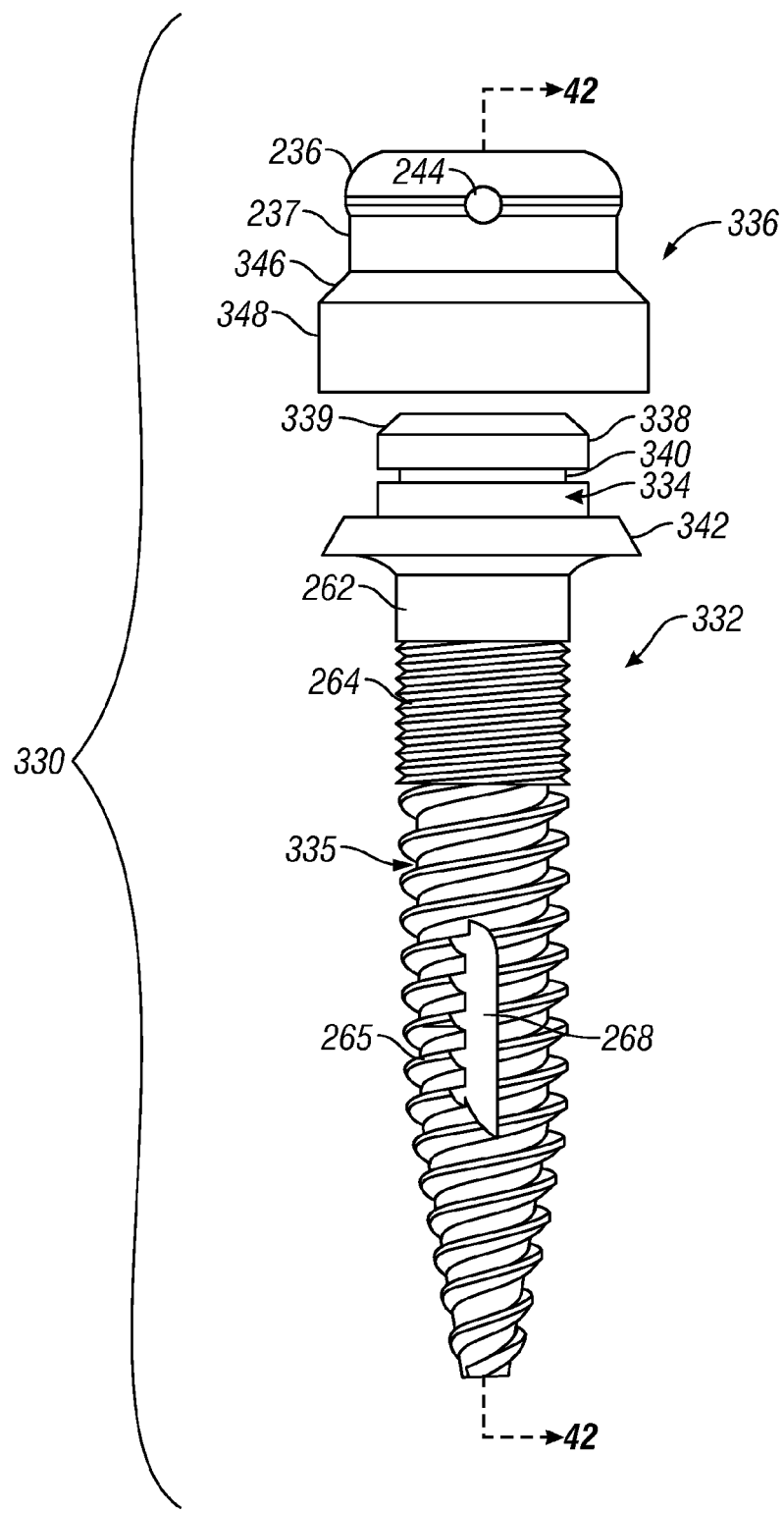
FIG. 41 is an exploded side elevation view of a taper press fit two part mini implant according to another embodiment, with the parts of the implant separated.

FIGS. 39 and 40 illustrate another embodiment of a two piece implant 310 which has an internal threaded attachment between the parts, as in the previous embodiment. The implant 310 is similar to the implant 290 of the previous embodiment, and like reference numbers have been used for like parts as appropriate. However, in this embodiment, the enlarged lower part of the end portion of the abutment head is removed, and the head portion of the main body has a taller cuff area, while the line of attachment between the parts is higher than in the previous two embodiments, as described in more detail below.

As illustrated in FIGS. 39 and 40, implant 310 comprises a main body 312 which is designed to be implanted in a patient's jaw in the manner described above in connection with the first embodiment, and an abutment head 314 designed for releasable attachment to the main body via a threaded shaft 306 which engages a threaded inner end portion 304 of the bore 300 in main body 312, in a similar manner to that described above in connection with FIGS. 36 to 38. The main difference between the main body 312 of this embodiment and the main body of the previous embodiment is that body 312 has a head or end portion with a longer outer cuff portion 315, and the upper end has an outer bevel 316 which surrounds the beveled inner rim 299 of the upper cup shaped seat 298. Main body 312 is otherwise identical to main body 292 of the previous embodiment, and like references have been used for like parts as noted above.

The part of the cuff region which was provided on the abutment head in the previous embodiments (i.e. outer annular region 238 along with the upper tapered portion 240) is eliminated from the abutment head in this embodiment, and instead the entire cuff portion 315 is located on the head of the main body, along with the upper bevel 316 which corresponds to bevel 240 in the previous two embodiments. The abutment head 314 in this embodiment therefore has an end portion which terminates with an annular, downwardly facing bevel 320 at the lower end of waist or indented portion 237 which corresponds to the lower bevel 242 of the previous embodiment. Thus, portions 240 and 238 of the abutment heads of the previous two embodiments are eliminated and instead are provided on the head of the main body (upper part of cuff region 315 and outer bevel 316). Other portions of the abutment head 314 are identical to the previous embodiments, and like reference numbers are used for like parts as appropriate.

In this embodiment, the abutment head 314 is removably secured to the main body in the same manner as described above in connection with the previous embodiment. Shaft 306 is inserted in bore 300 and the lower threaded end portion of the shaft is threaded into the threaded lower portion 304 of bore 300 so that the lower part of enlarged end portion 318 seats in cup shaped seat 298 with the lower bevel 320 engaging the beveled inner rim 299 of seat 298. In this embodiment, the line of separation or connection between the two parts is located at point 322, i.e. above the tissue level 324 defined by the upper end of tissue cuff 315. As in the previous embodiments, the lower end of cuff 315 defines the approximate bone level 325 below which the shaft 295 of the main body engages in endosseous bone.

In the two previous embodiments, the line of connection between the main body and the abutment member or head is located in the cuff region (see reference number 260 in FIGS. 31 and 32 and in FIG. 35), and thus below the tissue level (see FIG. 32). The advantage of the design in FIGS. 39 and 40 is that the line of connection between the two parts of the implant is not located in the cuff region of the implant, but instead is totally separate and above the surrounding tissue or gum, eliminating any junction along the outer diameter of the tissue cuff, so that the abutment member or head can be replaced by the dentist without any disturbance of the tissue.

FIGS. 41 to 44 illustrate another embodiment of a two piece implant 330 in which the threaded connection between the parts is replaced with a taper press or taper lock fit between the parts. Some portions of the two piece implant 330 of this embodiment are identical to equivalent portions of the previous embodiments, and like reference numbers have been used for like portions as appropriate. Two piece implant 330 comprises a main body 332 which has a modified upper end portion 334 and a shaft 335, and an abutment head 336. The shaft 335 is designed for osseointegration in a prepared bore in a patient's jaw bone and has similar threaded regions to the shafts 114 and 295 of the previous embodiments, and like reference numbers have been used as appropriate. The upper end portion 334 has a hex bore 225 as in the first embodiment, while the threaded boss 224 of the first embodiment is replaced by a generally cylindrical upper portion 338 terminating in an upper taper or bevel 339. A cement groove 340 is located in the cylindrical upper portion, and an upwardly facing, outer taper fit portion 342 is located at the lower end of the cylindrical portion 338.

The abutment head 336 has a through bore as in the first embodiment, but the internal threads 230 are replaced by a cylindrical portion 344 followed by a lower taper fit portion 345 at the lower end of the through bore. Taper fit portion 345 faces the taper fit portion 342 on the first end portion of the main body 332. The taper of the two portions 342 and 345 match one another and are pressed onto the respective parts of the implant 330 during manufacture. In order to secure the two parts of the implant together, the abutment member bore is engaged over the cylindrical upper portion 338 of the main body and the parts are pressed together to produce a taper fit or taper lock between portions 342 and 345.

The upper end of the through bore in abutment head 336 comprises a socket 232 with an inner rounded rim 233 as in the previous embodiments which is designed for releasable snap engagement with the post or shaft 234 of a male or retention member 250 as illustrated in FIGS. 31 and 32. The outer surface of the abutment head has a rounded upper end 236 followed by an indented or waist portion 237 identical to that of the previous three embodiments, which together form an outer locating portion designed for releasable snap engagement with the skirt 258 of a male or retention member 250 as described above in connection with the embodiment of FIGS. 27 to 32. The waist portion 237 is followed by an outer tapered shoulder 346 and a cuff portion 348. Thus, in this embodiment, the entire cuff portion is located on the abutment head, unlike the previous three embodiments where only part of the cuff was located on the abutment head (embodiments of FIGS. 27 to 32 and 33 to 38), or the entire cuff was located on the head or end portion of the main body (embodiment of FIGS. 39 and 40).

Once the abutment head has been attached to the main body and the main body is sufficiently secured in the bone, a suitable male or retention member in a denture or dental appliance can be releasably attached to the abutment head, as described above in connection with the embodiment of FIGS. 27 to 32, and the appliance can be repeatedly snapped into and out of engagement with the abutment head as desired by the patient. If the attachment or locating surfaces of the abutment head become too worn for reliable attachment to mating male member in the dental appliance, the abutment head can be removed by the dentist using a tool that engages in the socket 232 and uses upward pressure rather than rotation to release the taper lock and disconnect the removable abutment head from the main body of the implant. This can be done without disturbing the implant, and a new abutment member can then be engaged over the head portion of the main body. Cement can be placed into the cement groove 340 before engaging the abutment head over the cylindrical portion 338 to allow the replacement abutment head to be cemented in place by the dentist.

FIGS. 45 to 49 illustrate another embodiment of a two piece mini implant 400. Mini implant 400 comprises a main body 402 with a first end portion 404 and an integral threaded post or shaft 405 extending from the first end portion, and a separate abutment head 406 which is removably securable to the main body. The implant is of identical or similar materials to the previous embodiments. In this embodiment, the abutment head 406 has an enlarged end portion 420 and a threaded post 418. The first end portion 404 of the main body has an external tool engaging formation 408 of hexagonal shape, rather than an internal hex portion 225 as in the previous embodiments, with taper or bevel 410 at the first end of the hex formation 408. An annular cuff 412 followed by an inwardly tapering portion 414 extends from the hex formation 408 to threaded post 405. Post 405 has three equally spaced arcuate indents or flutes 415, for self-tapping when the main body is threaded into a prepared bore in a patient's jaw bone. The first end portion 404 has an inwardly projecting, threaded bore 416 for threaded engagement with the threaded post 418 of abutment head 406.

Figure 49:
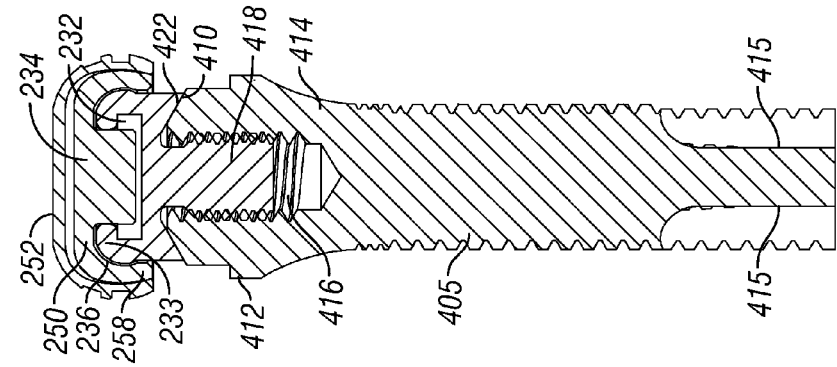
FIG. 49 is a longitudinal cross-sectional view on the lines 49-49 of FIG. 48.
Figure 48:
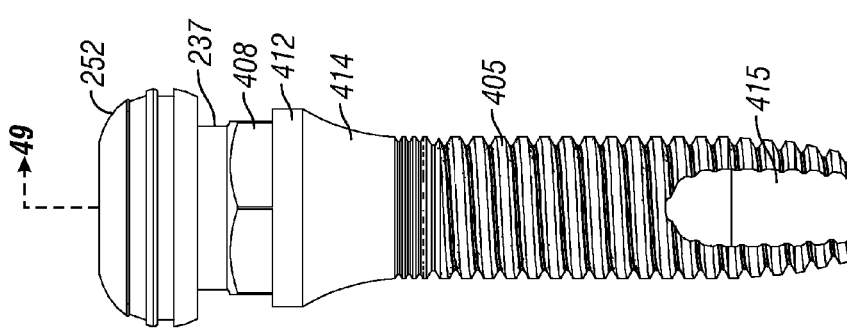
FIG. 48 is a side elevation view of the assembled parts of a dental anchor apparatus including the two part implant of FIGS. 45 to 47.
Figure 47:
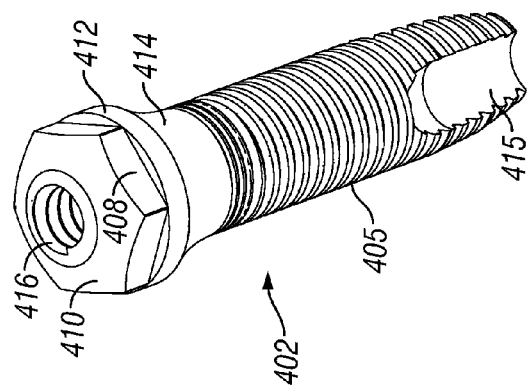
FIG. 47 is a perspective view of the main body of the implant of FIGS. 45 and 46, illustrating the external, tool engaging hexagonal formation.

Abutment head 406 is similar in some respects to the abutment head 318 of FIGS. 39 and 40, and like reference numbers are used for like parts as appropriate. However, the threaded post 418 is shorter, and the enlarged end portion 420 has an end face with a generally conical, inward taper 422 for engagement with the bevel or taper 410 at the first end of main body 402, as seen in FIG. 49. As in some of the previous embodiments, end portion 420 has a socket 232 with an inner rounded rim 233 which is designed for releasable snap engagement with the post or shaft 234 of a male or retention member 250 as illustrated in FIGS. 48 and 49. The outer surface of the abutment head has a rounded upper end 236 followed by an indented or waist portion 237 identical to that of FIGS. 27 to 32 and 35 to 40, which together form an outer locating portion designed for releasable snap engagement with the skirt 258 of a male or retention member 250, as seen in FIG. 49.

The main body 402 of the implant 400 is first installed in a prepared bore in a patient's jawbone, with the hex formation 408 gripped by a suitable hex driver tool or wrench which can be used to thread the post 405 into a prepared bore in the jaw bone, cutting threads into the bone as it is installed. The threaded post may be coated by any suitable coating material prior to installation, as is known in the field of endosseous implants. The abutment head may be secured to the main body before performing this procedure, using a suitable tool or driver engaging in the socket 232 as described above in connection with the preceding embodiments. The post 418 is threaded into bore 416 until the tapered lower face 422 of the upper end portion is seated against bevel 410, reduce lateral stress on the thread connecting the two parts.

After osseointegration is complete, the abutment head is engaged with a cap male or retention member 250 which is in swivel engagement in a cap 252, as illustrated in FIGS. 48 and 49. Cap 252 is secured in a recess in a denture or dental appliance in the same way as illustrated in FIG. 32 for the embodiment of FIGS. 27 to 32. In FIGS. 48 and 49, the retention member 250 is in hinging, snap engagement in cap 252 and releasably snap engaged over the outer locating surface portion 236 of abutment head 406. At the same time, post or shaft 234 is in snap engagement in socket 232.

In another embodiment of a two-piece implant, the outer locating surface on the abutment head may have a first set of at least two axially spaced snap engaging formations while the inner locating surface of the retention member has a second set of at least two axially spaced snap engaging portions for releasable snap engagement with the snap engaging formations on the locator, as illustrated for a one-piece implant in the embodiment of FIGS. 22 to 26. One of the sets of snap engaging formations may comprises spaced annular projections or ribs on one of the locating surfaces while the other set comprises spaced annular grooves for snap engagement over the annular projections or ribs. The post may be omitted in this embodiment, or the post may be included for additional assistance in aligning the dental appliance when placed in the mouth.

In each of the embodiments of FIG. 27 to 49, a two piece mini implant has a separate, removably attached abutment head designed for snap engagement with a retention member retained in a cap in a dental prosthesis. The main body can be directly implanted into a prepared bore in the jawbone. This expedites delivery of a finished denture, partial denture, or other dental prosthesis to a patient. At the same time, because the mini implant is made in two parts, the abutment head can be replaced as needed when the attachment or locating surfaces become too worn to work properly. This is an improvement over a one piece mini implant which would have to be completely removed and replaced with a new implant or altered to continue proper usage, requiring considerable time and expense.

Two or more one or two piece mini implants may be placed at selected locations in a patient's mouth, depending on the size and location of the dental prosthesis to be installed. Bores are first prepared at suitable locations in the jaw bone, and the threaded shafts of the main bodies of the implants are threaded into the bores. The shafts or posts may first be treated with suitable coating and/or adhesive materials. Once installed, the locating portions of the abutment heads project above the bone and the gum level for snap engagement in opposing retention members which are in swivel engagement with caps secured in the dental appliance. The resilient nylon or plastic retention members remain in static engagement with the abutment heads of the implants when the appliance is in place, while the metal caps have a full range of rotational or swivel movement over the retention members while the dental appliance is in use, and can compensate for any misalignment between implants. At the same time, the wearer can readily remove the appliance by snapping the retention members off the locating portions of the abutment heads as necessary for cleaning purposes, and can easily replace the appliance by urging the retention members onto the abutment heads of the aligned implants until they snap into place.

The abutment heads of the above embodiments are designed for both inner and outer snap engagement with a mating male or retention member in a dental appliance which has an outer skirt for snap engagement over an outer locating surface on the abutment head and an inner post for snap engagement in the upper end socket in the abutment head. However, different abutment heads may be provided which have different attachment or locating surfaces designed for engagement with other types of male or retention members. In one embodiment, the inner locating surface of the skirt and the outer locating surface portion of the abutment head have interengageable snap formations and the retention member is releasably snap engaged over the abutment head. Both an inner snap engagement between the post and socket and an outer snap engagement between the cavity and outer locating portion of the abutment head may be provided in other embodiments, as described above in connection with the drawings, while in others only an inner snap engagement is provided.

The main body of the implant in the above embodiments has a shaft designed for threaded engagement in a bore in the jaw bone and subsequent osseointegration in the jaw. In alternative embodiments, different types of thread may be used, the thread cutting flats may be removed, or the threads may be replaced with other types of engagement formations for attachment in the bone.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A dental assembly comprising:
   a) an endosseous dental implant comprising:
      (i) a first end portion having a top and a bottom, the first end portion comprises:
         (1) an external projection extending from the top of the first end portion for releasable engagement with an abutment member, wherein the abutment member has an external lower bevel portion; and
         (2) an annular cuff portion defining an annular seat having a recessed, inwardly tapered bevel surface, wherein the tapered bevel surface surrounds the external projection; and wherein the lower bevel of the abutment contacts and seats on tapered bevel surface of the annular seat to form a line of connection when the abutment member is releasably engaged with the external projection, wherein the line of connection is located slightly below a patient's gum line when the implant is secured in the mouth of the patient; and
      (ii) a threaded post which extends from the bottom of the first end portion for direct engagement into the patient's bone or tissue; and
   b) an abutment with an internally threaded bore for threadable engagement with the external projection.

2. A dental assembly comprising:
   a) an endosseous dental implant comprising:
      (i) a first end portion having a top and a bottom, the first end portion comprises:
         (1) an external projection extending from the top of the first end portion for releasable engagement with an abutment member, wherein the abutment member has an external lower bevel portion; and
         (2) an annular cuff portion defining an annular seat having a recessed, inwardly tapered bevel surface, wherein the tapered bevel surface surrounds the external projection; and wherein the lower bevel of the abutment contacts and seats on tapered bevel surface of the annular seat to form a line of connection when the abutment member is releasably engaged with the external projection, wherein the line of connection is located slightly below a patient's gum line when the implant is secured in the mouth of the patient; and
      (ii) a threaded post which extends from the bottom of the first end portion for direct engagement into the patient's bone or tissue;
   b) an abutment; and
   c) a cap to be secured in a recess in a dental appliance, wherein the cap has an inner cavity for releasable engagement with the abutment.

3. A method of anchoring a dental appliance in a patient's mouth, comprising:
   a) securing one or more endosseous dental implant directly into a patient jaw bone; wherein the implant comprises:
      (i) a first end portion having a top and a bottom, the first end portion comprises:
         (1) an external projection extending from the top of the first end portion for releasable engagement with an abutment member, wherein the abutment member has an external lower bevel portion; and
         (2) an annular cuff portion defining an annular seat having a recessed inwardly tapered bevel surface, wherein the tapered bevel surface surrounds the external projection; and wherein the lower bevel of the abutment contacts and seats on tapered bevel surface of the annular seat to form a line of connection when the abutment member is releasably engaged with the external projection; and
(ii) a threaded post which extends from the bottom of the first end portion for direct engagement into the patient's bone or tissue;
b) engaging an abutment with the external projection of the implant; wherein the abutment has an internally threaded bore and the external projection has external threads for threaded engagement with the internally threaded bore; and wherein the line of connection is located is slightly below a patient's gum line when the implant is secured in the mouth of the patient: and
c) securing the dental appliance to the abutment.

4. An endosseous dental implant comprising:
a) a first end portion having a top and a bottom, the first end portion comprises:
(i) a threaded external projection extending from the top of the first end portion for releasable connection and threaded engagement with an abutment member, wherein the abutment member has a bore having a lower threaded end portion and an external lower bevel portion; and
(ii) an annular cuff portion defining an annular seat having a recessed, inwardly tapered bevel surface, wherein the tapered bevel surface surrounds the external projection; and wherein the lower bevel of the abutment contacts and seats on tapered bevel surface of the annular seat to form a line of connection when the abutment member is releasably engaged with the external projection, wherein the line of connection is located slightly below a patient's gum line when the implant is secured in the mouth of the patient; and
b) a threaded post which extends from the bottom of the first end portion for direct engagement into the patient's bone or tissue.

5. The implant of any of claims 4, wherein the threaded post comprises a single lead thread or multiple lead threads.

6. The implant of claim 4, wherein the threaded post comprises two successive threads of different pitch.

7. The implant of any of claims 4, wherein the threaded post comprises opposing axial cuts adapted for self-tapping into the patient's bone or tissue.

8. The implant of any of claims 4, wherein the dental implant has a maximum outside diameter between about 1.5 mm and about 4.0 mm.

9. The implant of any of claims 4, wherein the annular cuff portion may be of different heights to accommodate different tissue depths.

10. The implant of any of claims 4 wherein the external projection has a tool-receiving bore extending inwardly from the upper end of the projection.

* * * * *